US012440637B2

(12) United States Patent
Brown et al.

(10) Patent No.: US 12,440,637 B2
(45) Date of Patent: Oct. 14, 2025

(54) HEADGEAR

(71) Applicant: Fisher & Paykel Healthcare Limited, Auckland (NZ)

(72) Inventors: Kyle Gregory Brown, Auckland (NZ); Mark Arvind McLaren, Auckland (NZ); Bernard Tsz Lun Ip, Auckland (NZ); Mark Richard Tomlinson, Auckland (NZ); Chris Onin Limpin Hipolito, Auckland (NZ); Craig Robert Prentice, Auckland (NZ); Melissa Catherine Bornholdt, Auckland (NZ); Neil Gray Duthie, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 597 days.

(21) Appl. No.: 16/746,542

(22) Filed: Jan. 17, 2020

(65) Prior Publication Data

US 2020/0254208 A1 Aug. 13, 2020

Related U.S. Application Data

(63) Continuation of application No. 15/028,684, filed as application No. PCT/NZ2014/050005 on Oct. 17, 2014, now Pat. No. 10,576,234.

(Continued)

(51) Int. Cl.
*A61M 16/06* (2006.01)

(52) U.S. Cl.
CPC ..... *A61M 16/0683* (2013.01); *A61M 2210/06* (2013.01)

(58) Field of Classification Search
CPC .......... A61H 1/00; A61H 1/001; A61H 1/003; A61H 1/005; A61H 23/00; A61H 2023/002; A61H 23/006; A61H 23/02; A61H 2201/12; A61H 2201/1207; A61H 2201/1623; A61H 2201/1635;

(Continued)

(56) References Cited

U.S. PATENT DOCUMENTS 1,229,050 A 6/1917 Donald
2,126,755 A 8/1938 Dreyfus (Continued)

FOREIGN PATENT DOCUMENTS

AU 685668 1/1998
AU 2008906390 12/2008

(Continued)

OTHER PUBLICATIONS

English translation of DE 102006057763, machine translated by espacenet.com, translated on Jan. 17, 2025.*

(Continued)

*Primary Examiner* — Tu A Vo
(74) *Attorney, Agent, or Firm* — VIA LLP

(57) ABSTRACT

Headgear for a respiratory interface has multiple separate sections of material joined to form the headgear and different levels of resilient extensibility or stretchability in at least four different parts or straps of the headgear. The multiple separate sections of material can include a rear part, a pair of upper side straps, a pair of lower side straps, and a top strap.

24 Claims, 28 Drawing Sheets

Related U.S. Application Data

(60) Provisional application No. 61/978,381, filed on Apr. 11, 2014, provisional application No. 61/969,934, filed on Mar. 25, 2014, provisional application No. 61/892,878, filed on Oct. 18, 2013.

(58) Field of Classification Search
CPC .......... A61H 2201/0107; A61M 16/06; A61M 16/0605; A61M 16/0616; A61M 16/0633; A61M 16/0683; A61M 16/0688; A42B 1/00; A62B 18/00; A62B 18/02; A62B 18/04; A62B 18/08; A62B 18/084; A61F 5/56; A61F 9/02; A61F 9/027
See application file for complete search history.

(56) References Cited

U.S. PATENT DOCUMENTS

| | | | | |
|---|---|---|---|---|
| 2,199,690 | A * | 5/1940 | Bullard ................ | A62B 18/084 D24/110.2 |
| 2,353,643 | A | 7/1944 | Bulbulian | |
| 2,928,387 | A | 3/1960 | Layne | |
| 3,295,529 | A | 1/1967 | Stephen et al. | |
| 3,424,633 | A | 1/1969 | Corrigall et al. | |
| 3,457,564 | A | 7/1969 | Holloway | |
| 3,530,031 | A | 9/1970 | Loew | |
| 4,513,896 | A | 4/1985 | Hirsch | |
| 4,553,934 | A | 11/1985 | Armstrong et al. | |
| 4,739,757 | A | 4/1988 | Edwards | |
| 4,774,946 | A | 10/1988 | Ackerman et al. | |
| 4,793,032 | A * | 12/1988 | Crowle ................ | A44B 11/266 24/615 |
| 4,960,121 | A * | 10/1990 | Nelson ................ | A62B 18/025 D24/110.4 |
| 5,038,776 | A | 8/1991 | Harrison et al. | |
| 5,416,924 | A | 5/1995 | Sims | |
| 5,488,948 | A | 2/1996 | Dubruille et al. | |
| 5,517,986 | A | 5/1996 | Starr et al. | |
| 5,538,000 | A | 7/1996 | Rudolph | |
| 5,592,937 | A | 1/1997 | Freund | |
| D383,204 | S | 9/1997 | Lomas | |
| 5,724,965 | A | 3/1998 | Handke et al. | |
| 5,737,777 | A | 4/1998 | Hilleary | |
| 5,934,276 | A | 8/1999 | Fabro et al. | |
| 6,012,164 | A | 1/2000 | Deal, III | |
| 6,119,694 | A | 9/2000 | Correa et al. | |
| 6,226,844 | B1 * | 5/2001 | Lerra .................. | A44B 11/006 24/615 |
| 6,338,342 | B1 | 1/2002 | Fecteau et al. | |
| 6,418,929 | B1 | 7/2002 | Norfleet | |
| 6,422,238 | B1 * | 7/2002 | Lithgow ........... | A61M 16/0683 128/206.13 |
| 6,470,886 | B1 | 10/2002 | Jestrabek-Hart | |
| 6,678,925 | B1 * | 1/2004 | Howell .............. | A44B 11/2592 24/647 |
| 6,701,927 | B2 | 3/2004 | Kwok et al. | |
| 6,805,117 | B1 | 10/2004 | Ho et al. | |
| 6,823,870 | B1 | 11/2004 | Hill et al. | |
| D505,489 | S | 5/2005 | Sleeper | |
| 6,907,882 | B2 | 6/2005 | Ging et al. | |
| 7,036,508 | B2 | 5/2006 | Kwok | |
| 7,047,972 | B2 | 5/2006 | Ging et al. | |
| 7,178,528 | B2 | 2/2007 | Lau et al. | |
| 7,188,620 | B2 | 3/2007 | Amarasinghe | |
| 7,210,481 | B1 | 5/2007 | Lovell et al. | |
| 7,219,669 | B1 | 5/2007 | Lovell et al. | |
| 7,222,374 | B2 | 5/2007 | Musal et al. | |
| 7,296,575 | B1 | 11/2007 | Radney | |
| 7,357,136 | B2 | 4/2008 | Ho et al. | |
| 7,509,958 | B2 | 3/2009 | Amarasinghe et al. | |
| D595,841 | S | 7/2009 | Mcauley et al. | |
| 7,562,658 | B2 | 7/2009 | Madaus et al. | |
| 7,779,832 | B1 | 8/2010 | Ho | |
| 7,802,573 | B2 | 9/2010 | Amarasinghe | |
| 8,132,270 | B2 | 3/2012 | Lang et al. | |
| 8,573,201 | B2 | 11/2013 | Rummery et al. | |
| 8,636,005 | B2 | 1/2014 | Gradon et al. | |
| 8,695,601 | B2 | 4/2014 | Hitchcock et al. | |
| 8,950,404 | B2 | 2/2015 | Formica et al. | |
| 9,032,955 | B2 * | 5/2015 | Lubke ............... | A61M 16/0683 128/206.21 |
| 9,149,596 | B2 * | 10/2015 | Valcic ............... | A61M 16/0816 |
| 10,576,234 | B2 | 3/2020 | Brown et al. | |
| 2002/0117177 | A1 | 8/2002 | Kwok | |
| 2003/0051732 | A1 | 3/2003 | Smith et al. | |
| 2003/0196655 | A1 | 10/2003 | Ging et al. | |
| 2003/0196658 | A1 | 10/2003 | Ging et al. | |
| 2004/0025882 | A1 | 2/2004 | Madaus et al. | |
| 2004/0067333 | A1 | 4/2004 | Amarasinghe | |
| 2004/0073989 | A1 * | 4/2004 | Horn ................. | A61M 16/0683 2/9 |
| 2004/0083534 | A1 | 5/2004 | Ruiz et al. | |
| 2004/0112377 | A1 | 6/2004 | Amarasinghe et al. | |
| 2004/0149280 | A1 | 8/2004 | Semeniuk | |
| 2005/0039753 | A1 | 2/2005 | Schumacher | |
| 2005/0076913 | A1 | 4/2005 | Ho et al. | |
| 2005/0172969 | A1 | 8/2005 | Ging et al. | |
| 2006/0000476 | A1 | 1/2006 | Salem | |
| 2006/0081252 | A1 | 4/2006 | Wood | |
| 2006/0118117 | A1 | 6/2006 | Berthon-Jones et al. | |
| 2006/0118119 | A1 | 6/2006 | Berthon-Jones et al. | |
| 2006/0130844 | A1 | 6/2006 | Ho et al. | |
| 2006/0201514 | A1 * | 9/2006 | Jones ................ | A61M 16/0616 128/206.24 |
| 2006/0283461 | A1 | 12/2006 | Lubke et al. | |
| 2007/0130663 | A1 | 6/2007 | Lang et al. | |
| 2007/0175480 | A1 | 8/2007 | Gradon et al. | |
| 2007/0181135 | A1 | 8/2007 | Baker | |
| 2007/0186931 | A1 | 8/2007 | Zollinger et al. | |
| 2007/0235033 | A1 * | 10/2007 | Reier ................... | A62B 18/084 128/207.11 |
| 2008/0011305 | A1 | 1/2008 | Chandran et al. | |
| 2008/0047560 | A1 | 2/2008 | Veliss et al. | |
| 2008/0060648 | A1 | 3/2008 | Thornton et al. | |
| 2008/0060745 | A1 | 3/2008 | Lau et al. | |
| 2008/0110466 | A1 | 5/2008 | Armitstead | |
| 2008/0142015 | A1 | 6/2008 | Groll | |
| 2009/0044808 | A1 | 2/2009 | Guney et al. | |
| 2010/0000544 | A1 | 1/2010 | Blaszczykiewicz et al. | |
| 2010/0031963 | A1 | 2/2010 | Lee et al. | |
| 2010/0043800 | A1 * | 2/2010 | Omura .................. | A61M 16/06 128/207.13 |
| 2010/0083961 | A1 | 4/2010 | Mcauley et al. | |
| 2010/0229868 | A1 | 9/2010 | Rummery et al. | |
| 2010/0258132 | A1 | 10/2010 | Moore | |
| 2010/0258136 | A1 | 10/2010 | Doherty et al. | |
| 2010/0307502 | A1 | 12/2010 | Rummery et al. | |
| 2011/0072553 | A1 | 3/2011 | Ho | |
| 2011/0197341 | A1 | 8/2011 | Formica et al. | |
| 2011/0197893 | A1 * | 8/2011 | Ziv .................. | A61M 16/0633 128/207.13 |
| 2011/0220113 | A1 * | 9/2011 | Newman ........... | A61M 16/0683 128/206.24 |
| 2011/0253143 | A1 | 10/2011 | Ho et al. | |
| 2011/0259337 | A1 * | 10/2011 | Hitchcock ......... | A61M 16/0875 128/207.11 |
| 2012/0101417 | A1 | 4/2012 | Joseph | |
| 2012/0138061 | A1 * | 6/2012 | Dravitzki .......... | A61M 16/0633 128/205.25 |
| 2012/0145158 | A1 | 6/2012 | Lubke et al. | |
| 2013/0008449 | A1 * | 1/2013 | Busch ............... | A61M 16/0683 128/206.21 |
| 2013/0213400 | A1 | 8/2013 | Barlow et al. | |
| 2014/0026888 | A1 * | 1/2014 | Matula, Jr. ............ | A61M 16/06 128/205.25 |
| 2014/0190486 | A1 | 7/2014 | Dunn et al. | |
| 2014/0209098 | A1 | 7/2014 | Dunn et al. | |

(56) References Cited

U.S. PATENT DOCUMENTS

2014/0305439 A1* 10/2014 Chodkowski ..... A61M 16/0605 128/207.11
2020/0254208 A1 8/2020 Brown et al.

FOREIGN PATENT DOCUMENTS

| | | | | |
|---|---|---|---|---|
| AU | 2009900327 | | 1/2009 | |
| AU | 2009902731 | | 6/2009 | |
| AU | 2009904236 | | 9/2009 | |
| AU | 2014334947 | | 4/2015 | |
| CA | 2671591 | | 6/2008 | |
| CN | 101237902 | | 8/2008 | |
| CN | 100415322 | | 9/2008 | |
| CN | 101432039 | | 5/2009 | |
| CN | 101553270 | | 10/2009 | |
| CN | 102245250 | | 11/2011 | |
| CN | 102458547 | | 5/2012 | |
| CN | 103153379 | | 6/2013 | |
| CN | 103619393 | | 3/2014 | |
| DE | 817734 | C * | 4/1952 | |
| DE | 19548380 | | 7/1996 | |
| DE | 19962515 | | 6/2002 | |
| DE | 10254399 | | 6/2004 | |
| DE | 102006057763 | A1 * | 2/2008 | ........ A61M 16/0633 |
| EP | 1057494 | | 12/2000 | |
| EP | 1890755 | | 2/2008 | |
| EP | 2373368 | | 10/2011 | |
| GB | 880942 | | 10/1961 | |
| GB | 2264647 | | 9/1993 | |
| GB | 2268388 | | 1/1994 | |
| GB | 2454791 | A * | 5/2009 | ........ A61M 16/0683 |
| JP | H1025613 | | 1/1998 | |
| JP | 3602117 | | 5/2004 | |
| JP | 2005534383 | | 11/2005 | |
| JP | 2006505373 | | 2/2006 | |
| NZ | 595935 | | 5/2013 | |
| WO | WO 00/50122 | | 8/2000 | |
| WO | WO 00/74758 | | 12/2000 | |
| WO | WO 02/07806 | | 1/2002 | |
| WO | WO 02/47749 | | 6/2002 | |
| WO | WO 2004/012803 | | 2/2004 | |
| WO | WO 2004/041341 | | 5/2004 | |
| WO | WO 2004/041342 | | 5/2004 | |
| WO | WO 2005/028010 | | 3/2005 | |
| WO | WO 2005/032634 | | 4/2005 | |
| WO | WO 2005/039680 | | 5/2005 | |
| WO | WO 2005/076874 | | 8/2005 | |
| WO | WO 2005/079726 | | 9/2005 | |
| WO | WO 2006/044120 | | 4/2006 | |
| WO | WO 2006/072128 | | 7/2006 | |
| WO | WO 2006/127031 | | 11/2006 | |
| WO | WO 2006/130903 | | 12/2006 | |
| WO | WO 2006/133012 | | 12/2006 | |
| WO | WO 2006/138334 | | 12/2006 | |
| WO | WO 2007/006089 | | 1/2007 | |
| WO | WO 2007/147088 | | 12/2007 | |
| WO | WO 2008/007985 | | 1/2008 | |
| WO | WO 2008/030831 | | 3/2008 | |
| WO | WO 2008/068966 | | 6/2008 | |
| WO | WO 2009/026627 | | 2/2009 | |
| WO | WO 2009/052560 | | 4/2009 | |
| WO | WO 2009/059353 | | 5/2009 | |
| WO | WO 2009/148956 | | 12/2009 | |
| WO | WO 2010/066004 | | 6/2010 | |
| WO | 2011014931 | A1 | 2/2011 | |
| WO | WO 2012/140514 | | 10/2012 | |
| WO | WO 2013/026092 | | 2/2013 | |
| WO | WO 2013/050920 | | 4/2013 | |
| WO | WO 2013/064930 | | 5/2013 | |
| WO | WO 2015/006826 | | 1/2015 | |
| WO | WO 2015/057087 | | 4/2015 | |

OTHER PUBLICATIONS

English translation of DE 817734, machine translated by espacenet.com, translated on Jan. 17, 2025, translated on Jan. 17, 2025.*
U.S. Appl. No. 60/842,741, filed Sep. 7, 2006, Ho.
Answer of ResMed Corp. to Complaint for Patent Infringement and Counterclaims, *Fisher &Paykel Healthcare Ltd.* v. *ResMed Corp.*, Case No. 3:16-cv-02068-DMS-WVG (S.D. Cal.).
Certified Translation of PCT Publication No. WO 2008/068966.
Decision on Institution of Inter Partes Review Pending Case IPR2017-00340, Paper No. 8, May 16, 2017.
Declaration of Richard Lordo (Part1).
Declaration of Richard Lordo (Part 2).
Declaration of Richard Lordo (Part 3).
Transcript of Deposition of Geoffrey Sleeper taken Oct. 24, 2017.
FlexiFit 431 Full Face Mask, Specification Sheet, 2005.
Transforming Sleep, Forma Full Face Mask, Fisher & Paykel, 185045304 RevB. 2009.
Sulivan Nasal CPAP Products, Mask System Handbook, Sep. 1993.
Examination Report for Australian Application No. 2014334947 dated May 28, 2019 in 3 pages.
Combined Search and Examination Report; May 26, 2016; 5 pages.
UK Examination Report; Dec. 23, 2016; 3 pages.
China Examination Report; dated Jun. 1, 2017; 16 pages.
Australia Examination Report; dated Jun. 22, 2018; 3 pages.

* cited by examiner

HEADGEAR

INCORPORATION BY REFERENCE TO ANY PRIORITY APPLICATIONS

Any and all applications for which a foreign or domestic priority claim is identified in the Application Data Sheet as flied with the present application are hereby incorporated by reference under 37 CFR 1.57.

FIELD OF THE INVENTION

The invention generally relates to headgear for a respiratory interface.

BACKGROUND OF THE INVENTION

Respiratory interfaces or masks are used to provide respiratory gas or gases, such as air in CPAP therapy, including in for example VPAP and BiPAP systems, or NIV, or high flow rate therapy, for example.

A respiratory interface may comprise a nasal, oral, or full face, i.e. both nasal and oral, interface. In turn an interface may be an indirect interface which covers the nose, mouth, or both, or an indirect interface such as an interface comprising nasal nozzles or pillows or similar which enter into the nares of the wearer.

Headgear for a respiratory interface may comprise a pair of lower side straps which in use extend from a rear part of the headgear along the left and right sides of the user's head below the ears to connect to the interface, and a pair of upper straps which extend from the rear part of the headgear also along the left and right sides of the users head but above the ears, to connect to the interface. The upper straps may attach to the top of a forehead support extending upwardly from a frame of the interface to the wearer's forehead, or in an interface without a forehead support may extend downwardly from above the ears, below the eyes, to connect directly to the mask. Optionally headgear may also comprise a top strap such as a crown strap or a forehead strap, and respiratory headgear may be in various other forms. For example headgear may comprise only a crown or forehead strap or an occipital loop, and a single strap on either side of the user's head or face to the mask. Typically the length of one or more of the headgear straps is adjustable so that a user can don the interface and headgear when the headgear strap or straps are loose and then tighten the straps when the interface and headgear are in position, to hold the mask and headgear securely in position thereafter until removal or doffing.

Headgear is commonly formed at least in part from a soft flexible material such as a cloth covered foam material such a BREATH-O-PRENE™ material for example, but may be formed from other material such as in part or whole from a thermoplastic material for example.

SUMMARY OF THE INVENTION

An object of the invention is to provide headgear for a respiratory interface which is improved in at least one or more respects or at least provides the public or the medical profession with a useful choice.

In broad terms one aspect of the invention comprises headgear for a respiratory interface comprising at least four different levels of resilient extensibility or stretchability in at least four different parts or straps of the headgear, the headgear preferably comprising:

a rear part of the headgear,
a pair of upper side straps,
a pair of lower side straps, and
a top strap.

In broad terms another aspect of the invention comprises headgear for a respiratory interface comprising:

a rear part of the headgear,
a pair of upper side straps,
a pair of lower side straps, and
a top strap, composed of multiple separate sections of material joined to form the headgear, said separate sections comprising:

two upper side strap parts which form the upper straps, each including a curved rear portion, joined at the rear of the headgear to also form an upper rear strap,
a lower rear strap part which forms a lower rear strap; and
two lower side strap parts which form the lower side straps and are joined to the lower rear part on left and right sides; and wherein the headgear has comprises at least four different levels of resilient extensibility or stretchability in at least four different parts or straps of the headgear.

In broad terms another aspect of the invention comprises headgear for a respiratory interface comprising:

a rear part of the headgear,
a pair of upper side straps,
a pair of lower side straps, and
a top strap,
wherein the rear part or at least a lower portion of the rear part of the headgear and top strap have relatively highest stretchability, the pair of upper side straps are stretchable but have relatively less stretchability than the rear part of the headgear and top strap, and the pair of lower side straps have least stretchability or are substantially non-stretchable, or
wherein the upper side straps and top strap have relatively highest stretchability, the rear part or at least a lower portion of the rear part of the headgear has relatively less stretchability than the upper side straps and the top strap, and the pair of lower side straps has least stretchability or is substantially non-stretchable.

In broad terms another aspect of the invention comprises headgear for a respiratory interface comprising:

a rear part of the headgear,
a pair of upper side straps,
a pair of lower side straps, and
a top strap,
wherein the top strap has highest stretchability, the rear part or at least a lower portion of the rear part has relatively less and first intermediate stretchability, and the pair of upper side straps are stretchable but have relatively less again and a second intermediate stretchability, and the pair of lower side straps have least stretchability or are substantially non-stretchable, or
wherein the top strap has relatively highest stretchability, the pair of upper side straps has relatively less stretchability than the top strap, the rear part or at least a lower portion of the rear part of the headgear has relatively similar stretchability to the pair of upper side straps, and the pair of lower side straps have least stretchability or are substantially non-stretchable, or
wherein the top strap has highest stretchability, the pair of upper side straps are stretchable but have relatively less and a first intermediate stretchability, the rear part or at least a lower portion of the rear part has relatively less again and a second intermediate stretchability and the pair of lower side straps have least stretchability or are substantially non-stretchable.

In broad terms another aspect of the invention comprises a respiratory interface comprising seal or seal-shell, frame, and elbow components, and a headgear as described herein.

The headgear may comprise any one or more of the following features, in any combination.

Headgear for a respiratory interface useful herein may comprise on the ends of one or more straps a stop which inhibits the far end of the strap being withdrawn back through an opening in the interface and separating from the interface. Another part or parts of the headgear may be elasticated. A part or parts of the headgear may comprise a color or colors which provide(s) a visual cue to a user of an orientation in which the headgear is to be worn or donned. Headgear may comprise multiple sections joined to form the headgear including a stretchable crown strap and/or a lower rear strap and an upper rear strap separated across the rear of the headgear by a transverse opening.

In various embodiments the headgear may include at least one strap which connects to the interface or to another strap or part of the headgear by a near end portion of the strap passing through an opening in the interface or other strap or part of the headgear, with a far end of the strap beyond the near end portion enlarged or otherwise formed to inhibit the far end of the strap being withdrawn back through the opening in the interface or other strap or part (such as a connector) of the headgear.

In one embodiment the formed end of the strap may be enlarged. It may be enlarged perpendicular to a plane of the strap (when laid out flat) or in a plane of the strap or both. In one embodiment the enlarged end comprises a protrusion or boss (herein also: hardstop) formed on the far end of the strap. In one embodiment the headgear or at least said strap is formed from a soft flexible material such as a cloth covered foam material and the protrusion or boss is formed from a harder material, on the far end of the strap.

In another embodiment the formed end of the strap comprises a flexible or at least hingedly mounted (to the strap) tab (herein also: tabstop) formed on the end of the strap, on one or other sides of the strap or both. The far end of the strap beyond the near end, a near end portion of the strap opposite said far end, or both, may comprise a flexible or at least hingedly mounted tab. The hardstop or tabstop(s) on the end of the strap inhibits the end of the strap being pulled out of an opening in the interface or other strap or part of the headgear through which it passes. It inhibits the strap end from separating from the interface or other strap or part of the headgear through which it passes. Thus a user may loosen or open the headgear fully to make it as easy as possible to don the headgear with interface, without fear of the loose strap end(s) separating from the interface or other parts of the headgear. Similarly the user may loosen or open the headgear fully to remove or doff the headgear, again without fear of the strap(s) separating from the interface or other parts of the headgear. The opening in the interface may comprise an opening such as a slot-shaped opening in the interface or a part thereof such as a frame or shell part of the mask, for example, through which the strap end passes, and is captive by the hardstop or tabstop. An opening in another strap or part of the headgear may comprise an opening in a buckle of the headgear or a loop part of the headgear for example.

The strap or straps comprising the hardstop(s) or tabstop(s) may comprise a pair of lower side straps which in use extend from a rear part of the headgear along the left and right sides of the users head below the ears to connect to the interface, or a pair of upper straps to extend from a rear part of the headgear along the left and right sides of the users head above the ears to connect to the interface, or both, and/or a top strap such as a crown strap or a forehead strap. Upper straps may attach to the top of a forehead support extending upwardly from a frame of the interface to the wearer's forehead, or in an interface without a forehead support may extend from above the ears and below the eyes to connect to the mask. Alternatively the headgear may comprise only a crown or forehead strap or an occipital loop, and a single strap on either side of the user's head or face to the mask, which pass through openings on the mask and comprise hardstops at their far ends.

In at least some embodiments a strap or straps also comprise on a side of said near end portion of the strap opposite said far end, a second enlargement or flexible or at least hingedly mounted (to the strap) tab, to inhibit the strap beyond this second hardstop or tabstop passing through the opening in the interface or other strap or part of the headgear. This second hardstop or tabstop may be fixed to the strap like the far end hardstops or tabstops, or may be adjustable in position along the length of the strap and may comprise for example an adjustable clip.

In at least some embodiments a rear part of the headgear is resiliently extensible approximately in an axis of the strap(s) when the headgear is worn. For example the headgear may comprise a resiliently extensible section or strap or straps in the rear of the headgear. The resiliently extensible section or strap or straps may be an elasticated section or strap or straps for example.

In various embodiments a rear part of the headgear maintains separation between the upper and lower straps and/or structure or 'as worn' shape to the headgear.

In at least some embodiments lower straps and upper straps on each side of the headgear are connected by a structure element that maintains separation between the upper and lower straps and/or structure or 'as worn' shape to the headgear.

For example the upper and lower straps may be formed of a soft material substantially lacking structure or memory and the structure element on each side of the headgear may comprise a stiffer element having structure or memory, formed of a plastics material for example. The structure elements may be positioned on the headgear and shaped to extend behind the wearers ears when the headgear is worn. The structure elements may be positioned on the headgear and shaped to extend behind the wearers ears and also at least partly along the upper and/or lower straps, and/or at least partly along a forehead or crown strap of the headgear. The structure elements may be attached to the softer headgear material or straps by stitching or by bonding such as by ultrasonic or radio frequency (RF) welding or by gluing for example.

Alternatively or additionally the headgear may comprise resiliently extensible material attached to at least parts of the headgear or incorporated in the headgear when stretched to when relaxed provide shape to at least parts of the headgear.

In some embodiments the headgear may comprise non-flat shape memory in at least a lower loop of the headgear comprising all or at least part of the lower straps and the lower rear part of the headgear, or an upper loop of the headgear, or both.

In at least some embodiments an upper part or parts of the headgear or a lower part or parts of the headgear or both, or an interior or exterior of the headgear or both, or any other part of the headgear, comprise a color or colors or sign contrasting to or otherwise distinguishable from another part or parts of the headgear or a balance of the headgear or each other, which provides a visual cue to a user how the headgear with interface is to be worn or donned such as an orientation in which the headgear is to be worn or donned, or as to a top and/or bottom or an interior and/or exterior of the headgear.

In various embodiments the headgear may comprise an upper part or parts of the headgear or a lower part or parts of the headgear or both, or an interior or exterior of the headgear or both, comprising a color or colors or sign contrasting to or otherwise distinguishable from another part or parts of the headgear or a balance of the headgear or each other, which provides a visual cue to a user how the headgear with interface is to be worn or donned such as an orientation in which the headgear is to be worn or donned, or as to a top and/or bottom or an interior and/or exterior of the headgear. In such embodiments, the colours may be different colors or different tints, shades, tones, and/or hues of the same or similar color, such as but not limited to different shades of blue or grey.

In at least some embodiments a pair of lower straps to extend along left and right sides of a users head below the ears, and/or a lower part of a rear part of the headgear, comprise a color (a first color) indicative to a user that this is the bottom of the headgear and/or that this part of the headgear should be drawn over the users head by entering the user's head first through this lower part of the headgear.

In at least some embodiments a pair of upper straps to extend along left and right sides of a users head above the ears, and/or an upper part of a rear part of the headgear, and/or a top strap such as a crown strap or a forehead strap of the headgear, comprise a color (a second color) indicative to a user that this is the top of the headgear and/or that this part of the headgear should not be drawn over the users head first.

For example the first color and the second color may be contrasting or otherwise distinguishable colors. For example the first color may be green and the second color red or orange. In such embodiments, the colours may be different colors or different tints, shades, tones, and/or hues of the same or similar color, such as but not limited to different shades of blue or grey.

All of said parts of the headgear may comprise the first or second color or alternatively only for example edge or other portions.

In various embodiments the headgear comprises:

a rear part of the headgear, a pair of upper side straps, and a pair of lower side straps, composed of multiple separate sections of material joined to form the headgear, said separate sections comprising:

two upper side strap parts which form the upper straps, each including a curved rear portion, joined at the rear of the headgear to also form an upper rear strap, a lower rear strap part which forms a lower rear strap; and two lower side strap parts which form the lower side straps and are joined to the lower rear part on left and right sides.

In various embodiments the headgear comprises:

a rear part of the headgear, a pair of upper side straps, and a pair of lower side straps, composed of multiple separate sections of material joined to form the headgear, and wherein the rear part of the headgear comprises a lower rear strap and an upper rear strap separated across the rear of the headgear by a transverse opening.

In at least some embodiments the headgear also comprises a top strap and said separate sections include a top strap part.

In at least some embodiments the lower rear strap of the headgear is resiliently extensible or is more resiliently extensible than the upper rear strap of the headgear.

The headgear may also comprise a top strap such as a crown or forehead strap, which may be resiliently extensible or is more resiliently extensible than a balance of the headgear.

In various embodiments the top strap or top strap part may be resiliently extensible or is more resiliently extensible than a balance of the headgear.

In various embodiments the rear part of the headgear may be resiliently extensible or may be more resiliently extensible than a balance of the headgear but for the top strap.

In at least some embodiments the rear part of the headgear comprises a lower rear strap and an upper rear strap separated across the rear of the headgear by a transverse opening.

In at least some embodiments the upper side straps and the rear of the headgear define a closed loop which is less stretchable than the most stretchable top strap so that the top strap can accommodate different head sizes while the upper loop straps grip around the head to prevent the return or elastic resiliency of the top strap pulling the upper loop higher on the wearer's head after a wearer has donned and positioned the headgear on the wearer's head.

In at least some embodiments the upper side straps and upper rear strap of the headgear define an upper loop, the upper loop gripping around the head of a user sufficiently in use to prevent the return or elastic resiliency of the top strap pulling the upper loop higher on the user's head.

In at least some embodiments a rear part of each of the upper straps curves away from the top strap towards the rear part of the headgear.

In at least some embodiments a lower edge of the rear part of the headgear is scalloped towards an upper rear part of the headgear.

In various embodiments the headgear for a respiratory interface comprises:

a rear part of the headgear, a pair of upper side straps, a pair of lower side straps, and a top strap, wherein the headgear has at least four different levels of resilient extensibility or stretchability in four or more different parts or straps of the headgear.

In at least some embodiments four different sections of material from which the headgear is formed have four different levels of stretchability.

In at least some embodiments a rear part of the headgear or at least a lower rear part of the headgear, and the top strap, have relatively highest stretchability.

In at least some embodiments the top strap has higher stretchability than the rear or at least a lower rear portion of the rear part of the headgear.

In at least some embodiments the pair of upper side straps are stretchable but have relatively less stretchability than the rear part or at least the lower rear part of the headgear and top strap.

In various embodiments the lower rear strap is resiliently extensible or is more resiliently extensible than a balance of the headgear but for the top strap and the upper side straps.

In various embodiments the rear part of the headgear comprises a lower rear strap and an upper rear strap separated across the rear of the headgear by a transverse opening.

In various embodiments the lower rear strap is less resiliently extensible than the upper rear strap.

In various embodiments the lower rear strap is more resiliently extensible than the upper rear strap.

In various embodiments the upper side straps and the top strap have relatively highest stretchability.

In various embodiments the lower rear strap and the top strap have relatively highest stretchability.

In various embodiments the top strap has relatively highest stretchability.

In various embodiments the top strap has relatively highest stretchability, the upper side straps and the lower rear strap have an intermediate stretchability, and the lower side straps have the least stretchability.

In at least some embodiments the pair of lower side straps have least stretchability or are substantially non-stretchable.

In at least some embodiments the top strap is resiliently extensible, the upper side straps are less resiliently extensible than the top strap, the lower rear strap is less resiliently extensible than or substantially similarly resiliently extensible to the upper side straps, and the lower side straps are less resiliently extensible than the lower rear strap.

In at least some embodiments the upper side straps are formed of a first foam material having a first density;

the top strap is formed of a second foam material having a second density that is lower than the first density;

the lower rear strap is formed of a third foam material having a substantially similar density to the top strap but having a thickness that is greater than the thickness of the top strap; and the lower side straps are formed of a fourth foam material that has a lower extensibility or stretch than the first, second, and third materials, or is substantially non-stretch.

In at least some embodiments the top strap has the highest stretch;

the upper side straps have the next highest or a first intermediate stretch;

the lower rear strap has a substantially similar stretch to the upper side straps, or a lower again or second intermediate stretch; and the lower side straps have the lowest extensibility or stretch or are substantially non-stretch.

In at least some embodiments said separate sections of material joined to form the headgear comprise:

two upper side strap parts which form the upper straps, each including a curved rear portion, joined at the rear of the headgear to also form an upper rear strap, a lower rear strap part which forms a lower rear strap;

two lower side strap parts which form the lower side straps and are joined to the lower rear part on left and right sides; and a top strap part.

In at least some embodiments, at least some of said separate sections of material joined to form the headgear have been formed by cutting from cloth covered foam sheet material.

In at least some embodiments, at least some of said multiple separate sections have been formed by thermoforming an outline in cloth covered foam sheet material to define rounded edges in the subsequently cut out section, before cutting out the headgear section(s) to shape from the sheet material.

In at least some embodiments, at one or more, or a majority of, or all joins between any two of said separate sections of material joined to form the headgear the joined headgear sections overlap. The joined headgear sections may be joined through or at the overlap, by for example radio frequency welding the two headgear sections together, or by stitching or by bonding such as by ultrasonic welding or by gluing for example.

In at least some embodiments the join between each lower side strap part and the lower rear part is located such that in use each join will sit below and/or behind an ear of a user.

In at least some embodiments an area of relatively high friction material is located at each join and adapted to contact the user's head.

In at least some embodiments the headgear comprises at least one hook connector, the hook connector comprising an elongate tab portion, a hook portion, and a slot for removably receiving a strap located between the tab portion and the hook portion.

In at least some embodiments, the headgear for a respiratory interface comprises lower rear parts of the headgear positioned to be located when the headgear is worn below or towards the bottom of the ears and behind the ears but not as far back as the back of the neck, having relatively higher friction to inhibiting lower side straps of the headgear from riding up.

In broad terms another aspect of the invention comprises headgear for a respiratory interface comprising: end portions of straps comprising a section of fastening panel of hook material have a flexible tab, intermediate of the strap length, to fix the strap ends when the straps are tightened, or alternatively a matching section of loop material may be provided on the strap. Such headgear may also be used in any embodiment described herein.

The fastening panel may be located at the end of an upper side strap and/or a lower side strap.

On the upper side strap, the fastening panel may be located displaced from an end the upper side strap by a first spacing distance.

On the lower side strap, the fastening panel may be located displaced from an end of the strap by a second spacing distance greater than the first spacing distance, preferably great enough to allow the distal end to be grasped by a user without contacting or with little contact of fastening panel.

The fastening panel comprising the flexible tab may be attached to ends of upper and/or lower side strap by a substantially U-shaped partial peripheral seal that may be formed by gluing, stitching or welding fastening panel in place on material, preferably welding, preferably radio frequency welding.

The partial peripheral seal is typically of consistent width except for regions of greater area and an unsealed section at a portion of the fastening panel between the fastening panel and the flexible tab.

The relative arrangement of the regions of greater area and the unsealed section causes the flexible tab to extend from or stand proud of the upper side strap and/or lower side strap material, preferably with memory towards that position, such as an angle of about 10 to about 90°.

The configuration of the flexible tab is such that the flexible tab will engage with a hook connector as the upper side strap and/or lower side strap passes through a slot-shaped opening in, for example, a hook connector.

When the upper and/or lower side straps is not doubled back on itself and the strap end fixed down, the flexible tab will revert to the memorised position. The flexible tab thus also inhibits the end of the strap being pulled out of a slot.

Headgear or headgear and interfaces of the invention may be used in continuous positive airway pressure (CPAP) systems for providing a heated and optionally also humidified air stream to a user (U) through the interface worn by the user, or alternatively in other forms of respiratory systems, such as for example VPAP (Variable Positive Airway Pressure) systems, BiPAP (Bi level Positive Airway Pressure) systems, or in non-invasive ventilation (NIV), or high flow rate (not necessarily also above ambient pressure) therapy, for example, and are described herein generally with reference to CPAP therapy by way of example only. The headgear and interface may be useful particularly for CPAP therapy at air pressures in the range about 0.5 to about 40 cm $H_2O$. However the headgear or headgear and interfaces of the invention may also be used in systems or therapy in which the air or other gases are not heated and/or humidified.

In this specification the term "comprising" means "consisting at least in part of". When interpreting a statement in this specification and claims that includes "comprising", features other than that or those prefaced by the term may also be present. Related terms such as "comprise" and "comprises" are to be interpreted similarly.

BRIEF DESCRIPTION OF THE DRAWINGS

Embodiments of the invention are described with reference to the accompanying drawings, by way of example and without intending to be limiting, in which.

DETAILED DESCRIPTION OF EMBODIMENTS

Figure 1:
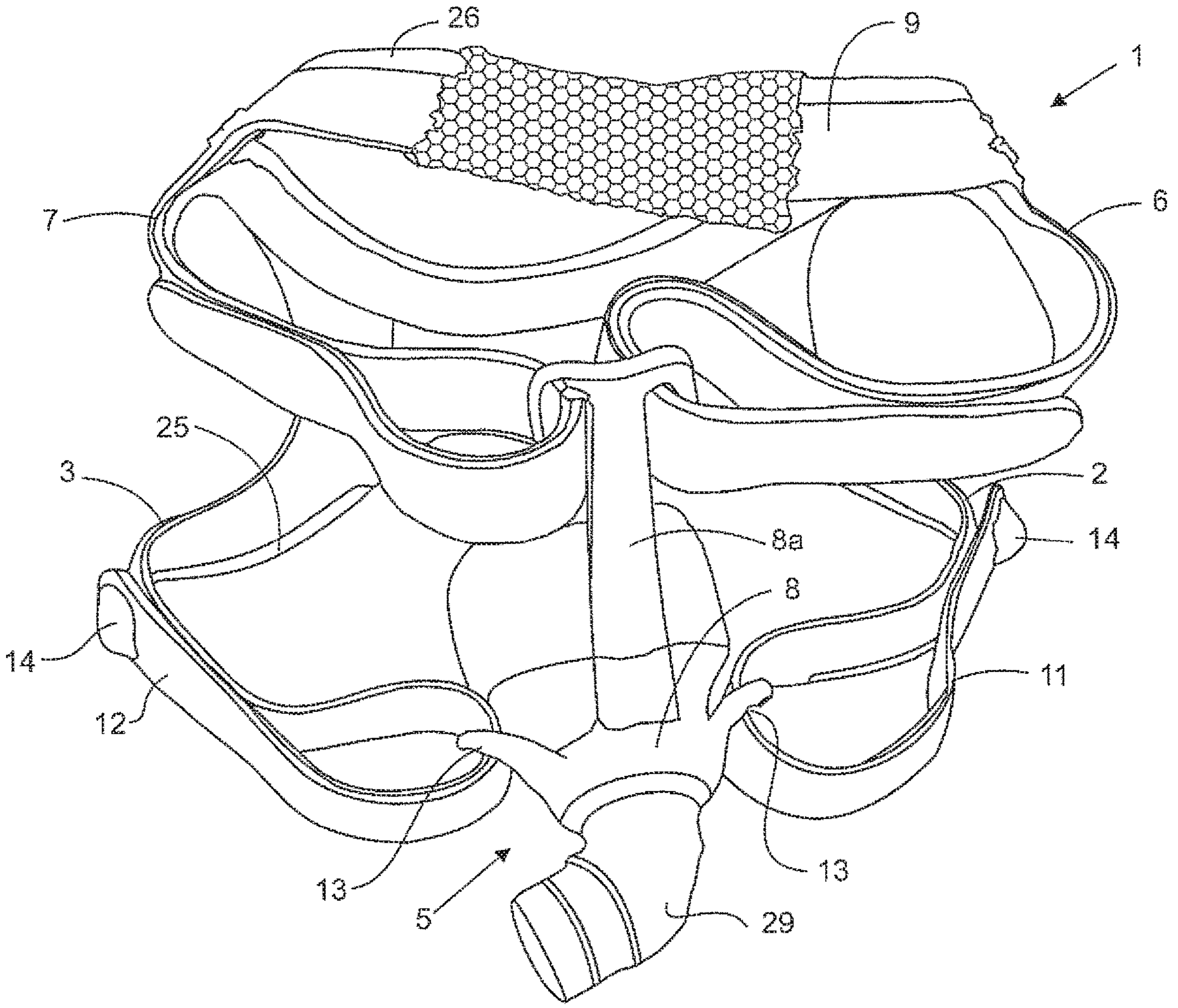
FIG. 1 is a front view of a first embodiment of headgear of the invention, and an (indirect) nasal interface, before being donned by a user.
Figure 2:
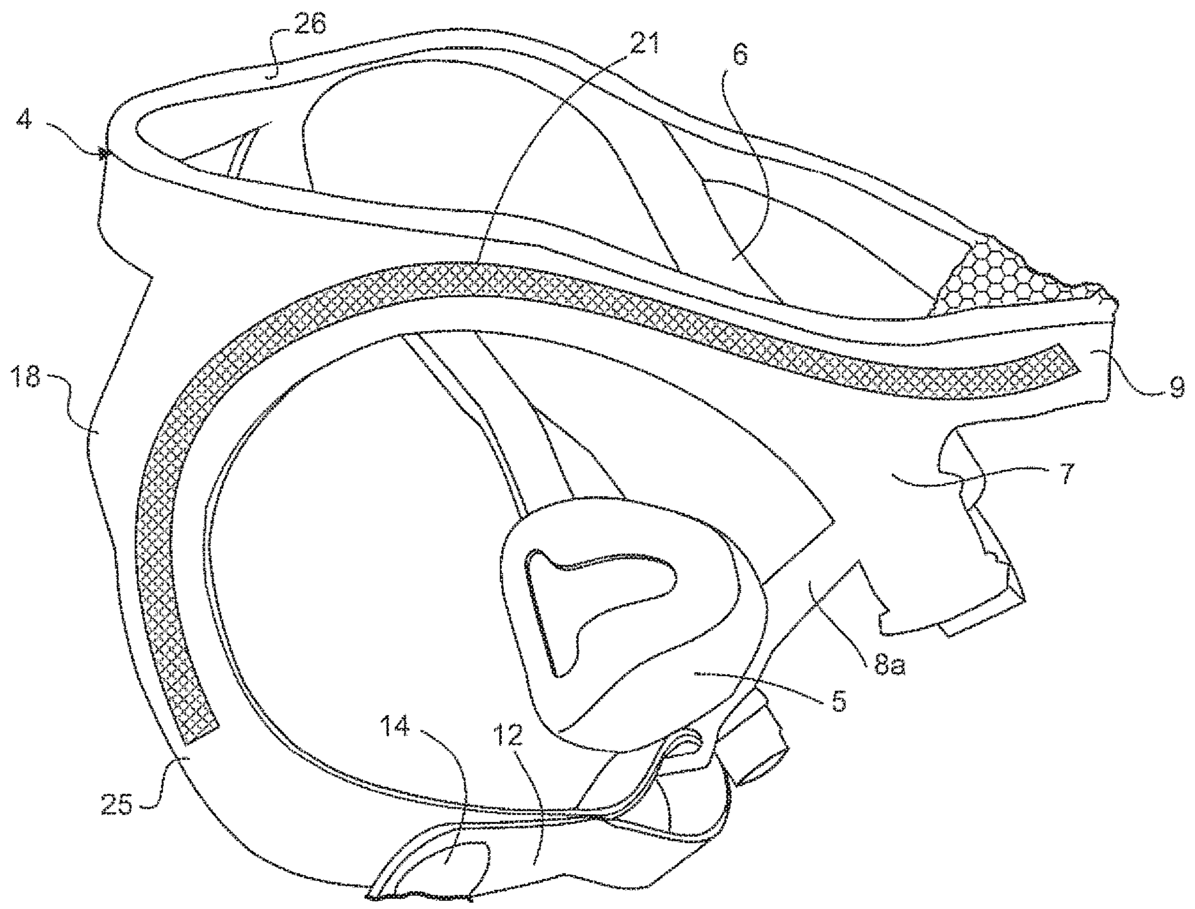
FIG. 2 is a left side view of the headgear of and interface of FIG. 1, again before being donned by a user.
Figure 3:
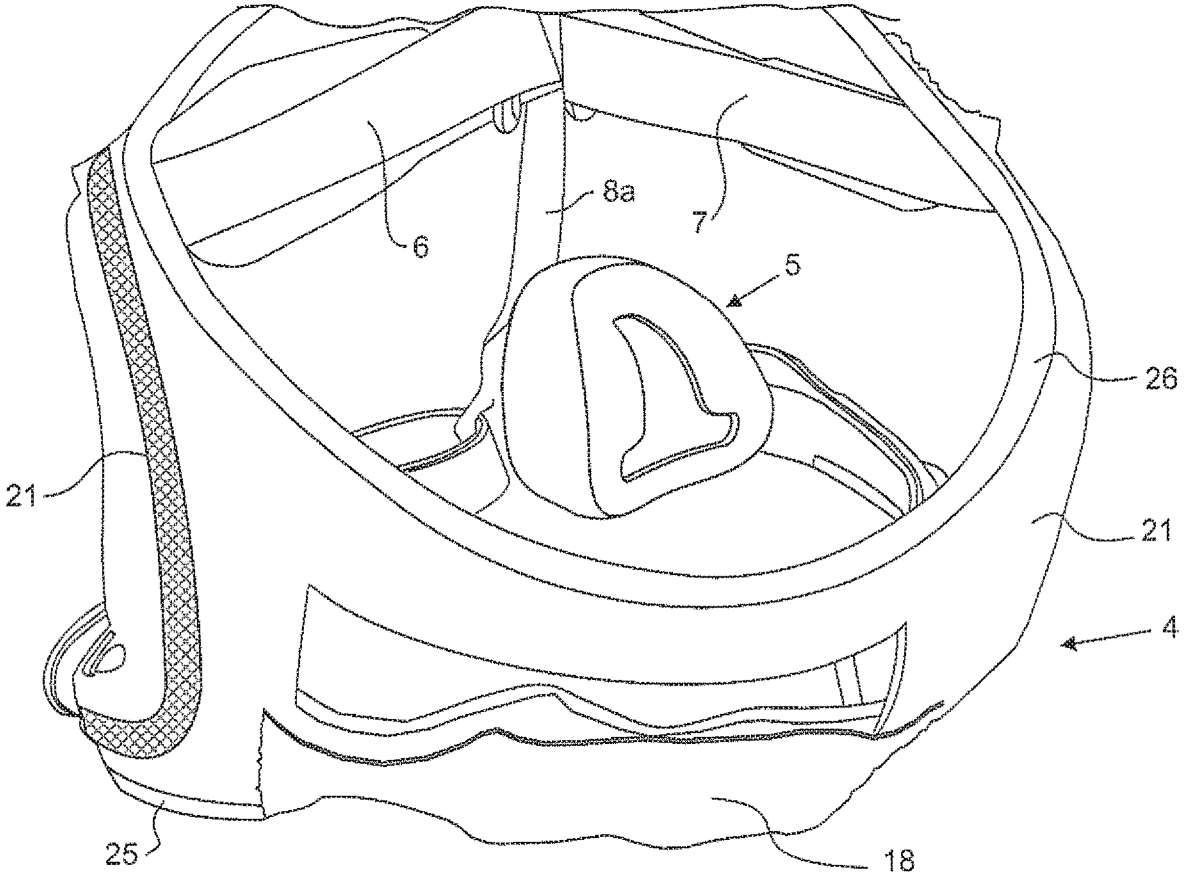
FIG. 3 is a rear view of the headgear of and interface of FIGS. 1 and 2, again before being donned by a user.

FIGS. 1 to 7E show headgear of a first embodiment and its use. Referring to FIGS. 1 to 3, the headgear 1 shown comprises left and right lower side straps 2 and 3 which when the headgear is worn extend from a rear part 4 of the headgear along the left and right sides of the users head below the ears to connect to interface 5, and a pair of left and right upper straps 6 and 7 which extend from a rear part of the headgear above the ears to connect to a forehead support 8*a* extending upwardly from a frame 8 of the interface to the wearer's forehead. The headgear also comprises a top strap 9 which may be a crown strap. In other embodiments the upper straps 6 and 7 may extend from above the ears and below the eyes to connect to the mask without a forehead support and/or the headgear may comprise a top strap in another form or no top strap. Typically the headgear is formed at least in part from a soft flexible material such as a cloth covered foam material such a BREATH-O-PRENE™ material for example. The interface in the embodiment shown is an indirect nasal interface but may in other embodiments be an oral or full face direct or an indirect interface (and a direct interface here includes a nasal cannula interface). Top strap 9 and/or upper straps 6 and 7 may be different colors, or different tints, shades, tones, and/or hues of the same or similar color, from the balance of the headgear, including but not limited to different shades of blue or grey.

Figure 4:
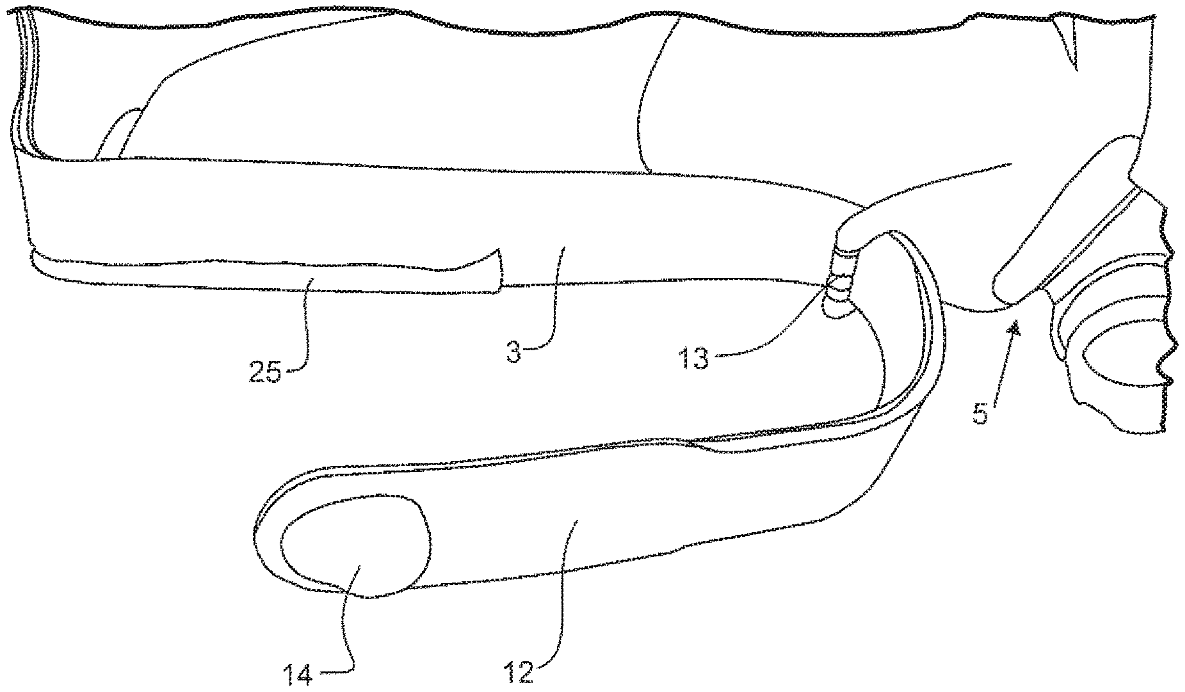
FIG. 4 is an enlarged view of the end of a right lower strap of the headgear of FIGS. 1 to 3, passing through an opening on a frame of the interface.

Referring particularly also to FIG. 4 the ends 11 and 12 of the lower straps 2 and 3 pass through slot-shaped openings 13 on left and right sides of frame 8 as shown (alternatively the straps may connect to frame 8 by hook connectors, through which the ends of the straps pass, as subsequently described with reference to FIGS. 10 to 14). The far ends 11 and 12 of the lower straps are enlarged as shown. The enlarged end of each strap comprises a protrusion or boss 14 (herein also: hardstop) formed on the far end 11 and 12 of each strap. The straps are formed from a soft flexible material such as a cloth covered foam material and the hardstop 14 is formed from a relatively harder material such as a harder plastics material or a TPE material or a resiliently compressible material. The enlarged end 14 of the straps may as shown be enlarged perpendicular to the plane of the strap (when laid out flat) but in any other way, or in a plane of the strap, or both. The near end portions of the straps comprise a section of hook material which may attach to a fabric surface layer of the straps at least on the outside surface of the strap (i.e. on the side of the strap opposite the patient side), intermediate of the strap length, to fix the strap ends when the straps are tightened, or alternatively a matching section of loop material may be provided on the strap. The hardstops 14 on the far ends of the straps inhibit the ends of the straps being pulled out of the opening 13 in the frame 8 (or other strap or part of the headgear) through which they pass. The hardstops 14 inhibit the strap ends from separating from the frame 8 even when loose. Thus a user may loosen or open the headgear fully to make it as easy as possible to don the headgear with interface, without fear of the strap(s) separating from the interface. By "inhibit", it is meant that the hardstops and/or tabstops impede but do not completely prevent the strap passing through its corresponding slot, and so make it difficult but not impossible for a user to pull the strap through its corresponding slot. In use, an intentional application of force to the strap will be sufficient to completely remove the strap from its corresponding slot but the act of donning and doffing the headgear will not be sufficient to remove the strap from its slot.

Figure 7A:
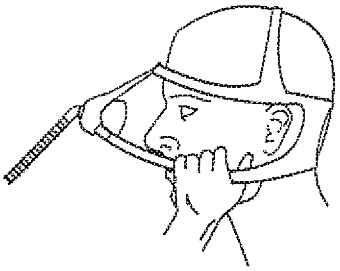
Figure 7B:
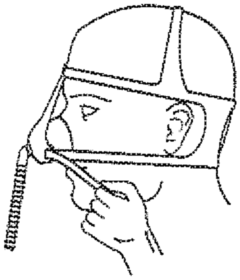
Figure 7C:
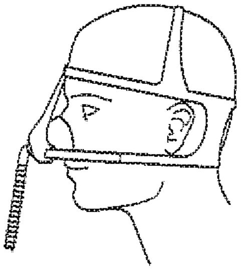

This is shown in FIGS. 7A-7C: FIG. 7A shows a person pulling the headgear with mask on—the user can pull the headgear on with the headgear fully open, i.e. the lower strap ends are not fixed back, or pull the headgear down, by the lower side straps 2 and 3 as shown in FIG. 7A without the ends of the lower side straps separating from the interface. While the headgear is being donned the hardstops 14 are against the frame openings 13 but cannot withdraw fully through these openings to separate from the frame. The user may pull the headgear on by the lower straps 2 and 3 for example, with the hardstops against the frame openings 13. The user then grasps the ends of the lower side straps 2 and 3 as shown in FIG. 7B and pulls them back to tighten the headgear and then fixes the ends back upon themselves as shown in FIG. 7C.

Figure 7D:
Figure 7E:
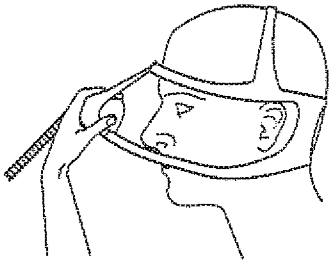
Figure 7F:
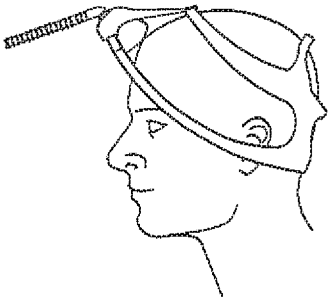
Figure 8:
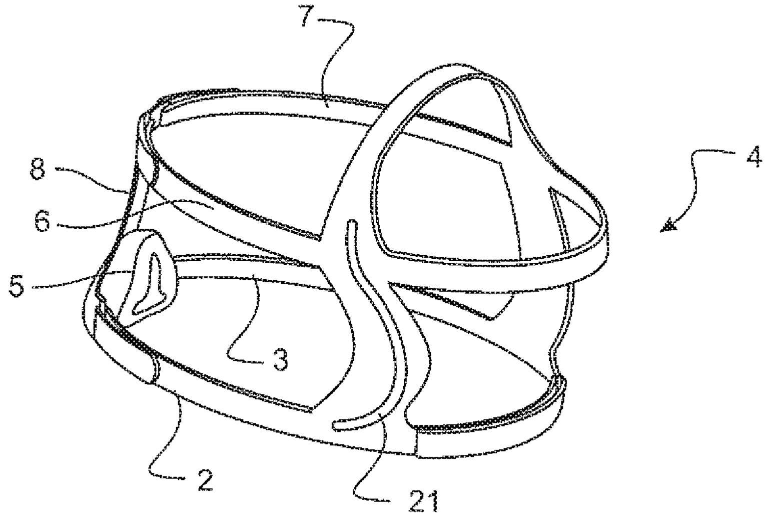
FIG. 8 is a left side view of a second embodiment of headgear of the invention.

FIGS. 7D-7E show the reverse steps in doffing the headgear. After the headgear has been loosened as shown in FIGS. 7D and 7E it can be pulled off as shown in FIG. 7E again without fear of the strap(s) separating from the interface.

Figure 6A:
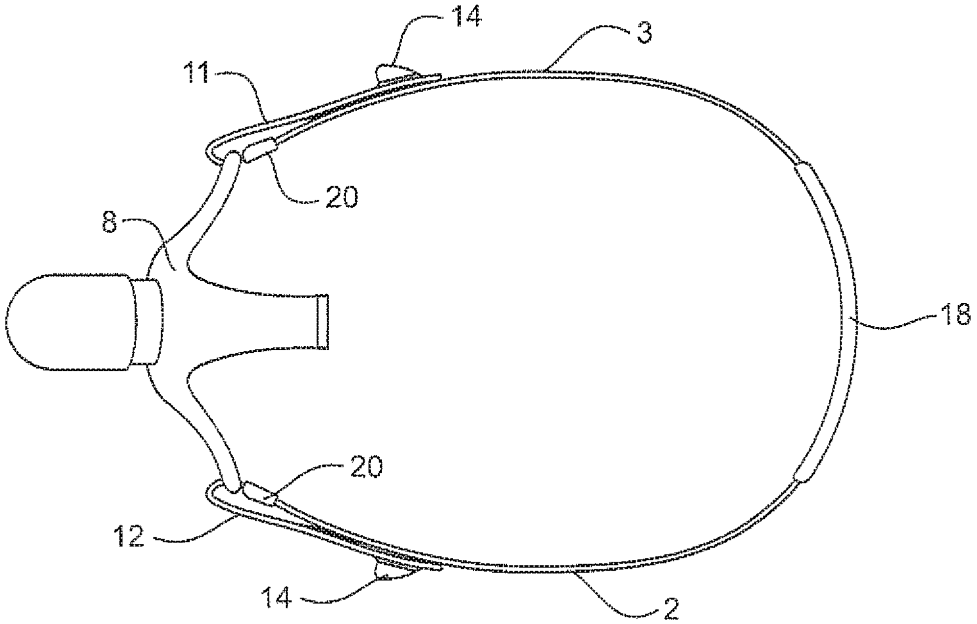
FIG. 6A is a view from above of the headgear and interface with the headgear open.
Figure 6B:
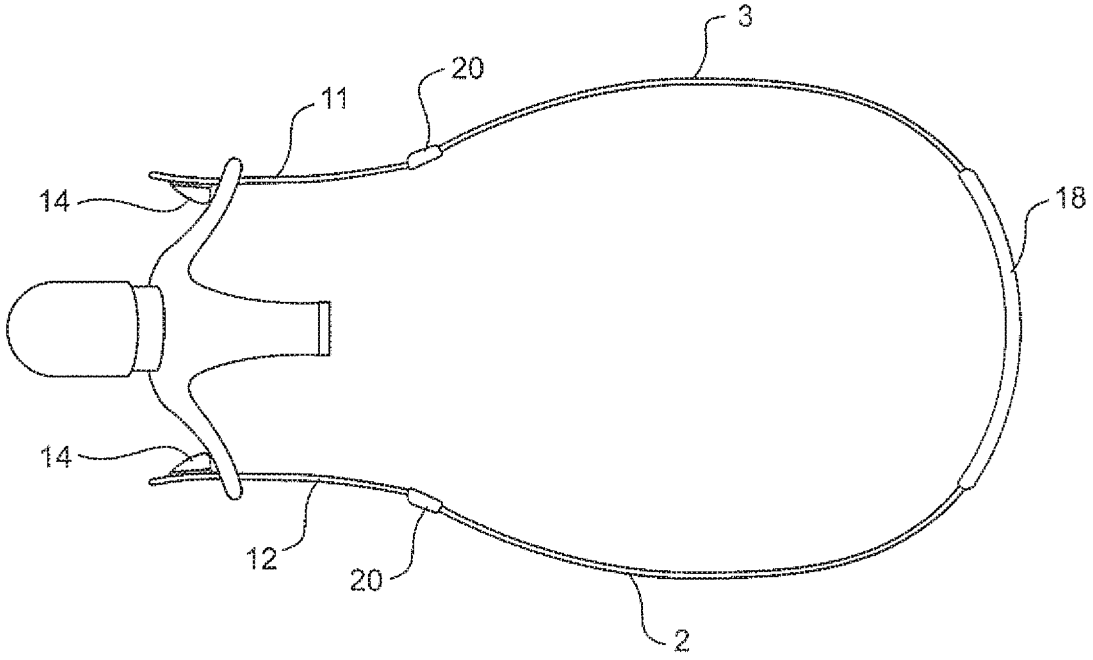
FIG. 6B is a view from above of the headgear and interface with the headgear tightened, FIGS. 7A-7C schematically show a series of steps in donning the headgear, FIGS. 7D-7E schematically show a series of steps in doffing the headgear.

FIG. 6A is a view from above of the headgear and interface with the headgear open, and FIG. 6B is a view from above of the headgear and interface with the headgear tightened.

In the embodiment shown a lower rear strap 18 of the headgear is elasticated so that in particular a 'lower loop' defined by the mask, the lower side straps 2 and 3, and the lower rear part 18 of the headgear can open up when pulled by a user over the head when donning the headgear (and the same when removing the headgear). This may enable a user to don the headgear without first loosening or opening the headgear as described above, i.e. in the embodiment shown above, the user leaves the straps 2 and 3 fixed back upon themselves in the position of last wearing of the headgear, instead of first releasing the straps so that the while donning the headgear the hardstops are against the frame as described above, and instead simply pulls the headgear down over the user's head, the elasticated section in the headgear stretching as needed as the user does so. The elasticated section allows the user to remove the headgear in the same way, i.e. by pulling back up over the head without first releasing the straps 2 and 3.

In the embodiment shown the rear part of the headgear comprises lower rear strap 18 which is elasticated as described and also an upper rear strap (which may or may not also be elasticated), but in an alternative embodiment the rear part of the headgear may comprise a single rear panel, which may or may not be stretchable, for example.

Also or alternatively, a part of the crown strap 9 may be similarly elasticated so that the forehead strap can accommodate different head sizes.

Additionally or alternatively similar hardstops may be formed on the far ends of the upper side straps 6 and 7 which pass through and connect to similar openings to those 13 on the lower part of the frame 8 but at the top of the forehead support 8*a*, or in another embodiment which connect direct to the mask or mask shell without a forehead support.

Additionally or alternatively a similar hardstop may be formed on the end of one side of an adjustable crown or forehead strap, which passes through a buckle or loop on the other side of the crown or forehead strap, or in an adjustable rear strap, for example.

The hardstops may be a contrasting color to the rest of the headgear.

Figure 5A:
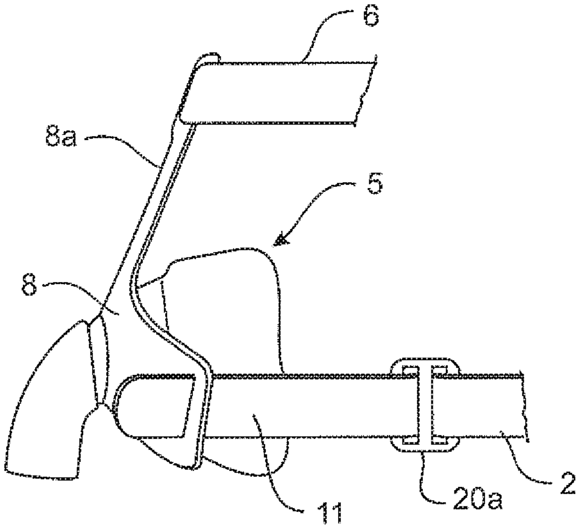
FIG. 5A is a part view of the left side of the headgear and interface, and the end of the right lower strap passing through an opening on a frame of the interface, with the headgear loose or open.
Figure 5B:
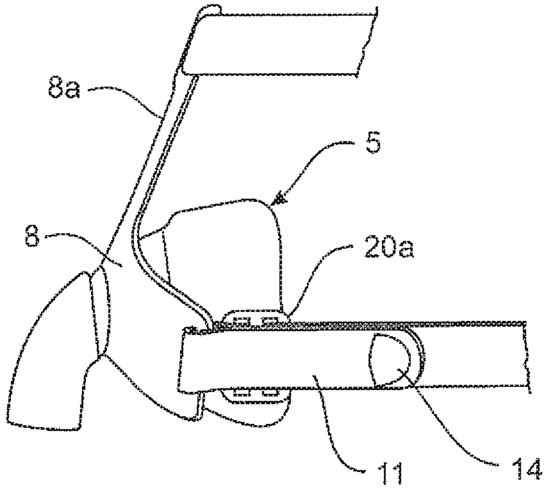
FIG. 5B is a part view of the left side of the headgear and interface, and the end of the right lower strap passing through an opening on a frame of the interface, with the headgear tightened.

Referring particularly to FIG. 6B the strap or straps 2 and 3 or 6 and 7 may also comprise on a side of said near end portion of the strap opposite said far end, a second enlargement 20 to inhibit the strap beyond this second enlargement passing through the opening 13 in the interface or other strap or part of the headgear. This second hardstop may be fixed and may be like hardstop 14 on the far end of the same strap, or may be adjustable in position along the length of the strap such as for example be an adjustable clip 20*a* as shown in FIG. 5A. A user may position such an adjustable second hardstop on each of the straps 2 and 3 or 6 and 7, along the strap so that when the strap is tightened to fit the user then this second hardstop will abut the frame and in particular the frame part defining the openings 13. Thus when the user is donning the mask and headgear and pulling the straps tight, in the step of FIG. 7B for example, the adjusted position-adjusted second hardstops act as place markers and the user need only pull the strap ends until the hardstops 20,20*a* hit the frame and then fix down the strap ends, and the headgear will be tightened with the same adjustment as before. This may be useful when donning the mask and headgear in the dark for example.

Referring to FIGS. 2 and 3, so that the headgear maintains separation between the upper and lower straps and/or structure or 'as worn' shape when not worn, i.e. before being donned, the headgear may comprise on each side of the headgear a structure element 21 between the lower and upper straps. For example the upper and lower straps or all of the headgear may be formed of a soft material substantially lacking structure or memory and the structure element on each side of the headgear may comprise a stiffer element having structure or memory, formed of a plastics material for example. A structure element 21 may positioned one on the headgear on each side, and shaped to extend behind the wearers ears when the headgear is worn. The structure elements 21 may also at least partly along the upper and/or lower straps, and/or at least partly along a forehead (or crown) strap of the headgear, as shown. The structure elements 21 may be attached to the softer headgear material or straps by stitching or bonding such as by welding or gluing for example. The structure elements 21 may have a segmented construction or otherwise be formed so that they are relatively more flexible in an approximately vertical plane than an approximately horizontal plane (both vertical and horizontal being when the headgear is worn by a user standing upright). The headgear structure may be such that the headgear does not lie without structure or shape when not worn but instead maintains a three dimensional structure or shape approximately similar to that of the headgear when worn. This may indicate to a user how the headgear is to be worn. The headgear may be formed to adopt this structure or shape when initially removed from its packaging (or from storage)—that is, if the headgear is constrained to a flatter or other shape when packaged, then memory built into the headgear for this shape causes the headgear to adopt this shape when removed from the constraints of the package (so that it is apparent to the user how the headgear is to be worn).

Figure 9A:
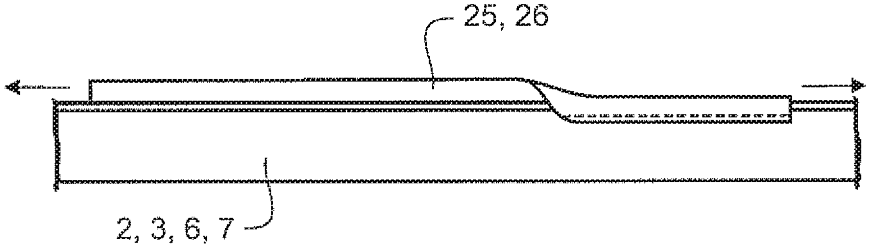
FIG. 9A shows part of an upper strap of headgear with edge piping comprising a contrasting color, and in an extended or stretched state.
Figure 9B:
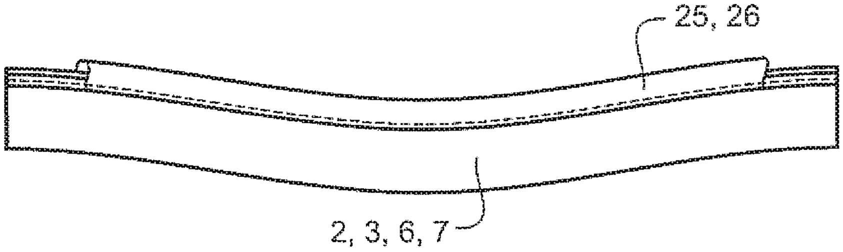
FIG. 9B shows the same part of an upper strap of headgear with edge piping of contrasting color, and in a relaxed state.

The edge piping 25 or equivalent such as colored strip material may be attached to its respective strap 2, 3, 6, 7 when the piping or strip material is stretched as shown in FIG. 9A, so that after attachment when the strap is relaxed the piping or strip material will tend to curve or add shape to the strap as shown in FIG. 9B. Edge or centrally applied strip material applied for this purpose—to add structure or shape to the headgear or headgear parts, may not necessarily also be of a contrasting color.

In at least some embodiments a 'visual loop' which includes the lower straps and the lower rear strap 18 of the headgear comprises edge piping 25 of a color which contrasts to or is otherwise distinguishable from a color of the rest of the headgear or other parts of the headgear, which may indicate to a user that this part of the headgear should be drawn over the users head first and/or with a particular orientation, and/or a top and/or bottom of the headgear. This part 25 of the headgear may be colored green for example. Upper part(s) 26 of the headgear may also or alternatively comprise a contrasting color to the rest of the headgear or other parts of the headgear such as a color of or on the lower part of the headgear, such as red or orange for example. These colors in these parts 25 and 26 of the headgear provide a visual cue to a user of the orientation in which the headgear with interface is to be worn or donned. Alternative to the colored edge piping of the embodiment shown the contrasting color may be in a colored material strip applied along, for example centrally along, the straps, or the material from which the straps are formed may be of a contrasting color, or the contrasting color may be printed on the headgear parts for example. Alternatively again, such edge piping or material strip may, instead of or additional to being contrastingly colored, comprise a different texture to the material from which the straps are formed. Such a different material, as an edge strip along one or more straps of the headgear, along an edge or one side, or centrally, may also additionally or alternatively comprise a structure element as previously described, to provide structure to the headgear. Additionally or alternatively an interior or exterior of the headgear or both may comprise contrasting one or more colors or signs indicating to a user an interior and/or exterior of the headgear. In such embodiments, the colours may be different colors or different tints, shades, tones, and/or hues of the same or similar color, such as but not limited to different shades of blue or grey.

The edge piping 25 or equivalent such as colored strip material may be resiliently extensible and may be attached to its respective strap when the piping or strip material is stretched as shown in FIG. 9A, so that after attachment when the strap is relaxed the piping or strip material will tend to curve or add shape to the strap as shown in FIG. 9B. Edge or centrally applied strip material applied for this purpose—to add structure or shape to the headgear or headgear parts, may not necessarily also be of a contrasting color. This may be in addition to or alternative to providing the structure elements 21 or similar on the headgear. That is, in other embodiments the headgear may be given shape or structure as described above in this may but without such structure elements 21 or similar. For example such resiliently extensible material attached to the headgear or incorporated in the headgear in at least a lower loop of the headgear comprising all or at least part of the lower straps and the lower rear part of the headgear, may cause this lower loop of the headgear to maintain or present a loop-like or at least non-flat shape when not worn for example when the headgear is placed on a bedside table, or other surface. The same may also or alternatively be applied to an upper loop of the headgear including the upper straps and upper rear part of the headgear. Further, such lower and upper parts of the headgear may be held separate by structure between them in the rear or sides of the headgear.

FIGS. 10 to 15 show headgear of a third embodiment.

FIGS. 17 to 22 show headgear of a fourth embodiment.

FIGS. 26 to 31 show headgear of a sixth embodiment.

In the third, fourth, and sixth embodiments, again the headgear 1 shown comprises left and right lower side straps 2 and 3 which when the headgear is worn extend from a rear part 4 of the headgear along the left and right sides of the users head below the ears to connect to interface 5, and a pair of left and right upper straps 6 and 7 which extend from a rear part of the headgear above the ears to connect to a forehead support 8*a* extending upwardly from a frame 8 of the interface to the wearer's forehead. The headgear also comprises a top strap 9 which may be a crown strap. In these embodiments the lower straps 2 and 3 connect to frame 8 by hook connectors 40 which pass through openings 41 on left and right sides of frame 8, preferably detachably and in a snap fit. The distal ends 11 and 12 of the lower straps 2 and 3 pass through slot-shaped openings 42 (see FIG. 10) in the hook connectors 40 as shown. The hook connectors 40 may be a snap fit (with an audible sound) onto the mask frame. The upper straps 6 and 7 connect to the forehead support 8*a* by passing directly through slot-shaped openings 144 at the top of the forehead support. Alternatively the upper straps 6 and 7 may also connect to forehead rest 8*a* by similar hook connectors 40 or alternatively again the lower straps may connect to the frame by passing directly through openings in the frame. Alternatively in other embodiments the upper straps 6 and 7 may extend from above the ears and below the eyes to connect to the mask without a forehead support and/or the headgear may comprise a top strap in another form or no top strap. Top strap 9 and/or upper straps 6 and 7 may be different colors, or different tints, shades, tones, and/or hues of the same or similar color, from the balance of the headgear, including but not limited to different shades of blue or grey.

The headgear may be formed from a soft flexible material such as a cloth covered foam material. The near end portions of the straps comprise a section of hook material which may attach to a fabric surface layer of the straps at least on the outside surface of the strap (i.e. on the side of the strap opposite the patient side), intermediate of the strap length, to fix the strap ends when the straps are tightened, or alternatively a matching section of loop material may be provided on the strap. In at least some embodiments the top strap 9 is resiliently extensible to accommodate different head sizes, for example by being elasticated, or is at least more resiliently extensible than the balance of the headgear which may be substantially inextensible or less extensible.

The rear part of the headgear comprises lower rear strap 18 and upper rear strap 44, with opening 45 transversely between them which extends across the lower back of the head and/or the neck when the headgear is worn, but in an alternative embodiment the rear part of the headgear may comprise a single rear panel. The headgear is formed so that the top strap 9, rear part of the upper straps 6 and 7, and the rear of the headgear particularly the upper rear strap 44 in the embodiment shown, define a closed loop (subject to any adjustment buckle being provided for example in the top strap 9) which when the headgear is worn encircles or cups the back or back and top-back of the user's head. The headgear may be formed so that when worn the rear part of the upper straps 6 and 7 curves towards the rear part of the headgear. That is, the upper straps may comprise a rear portion 6*a* and 7*a* curved towards the rear part of the headgear when the headgear is laid out flat (as shown in FIGS. 15, 22, and 31 to 33). Also, the lower edge 46 of the rear part of the headgear is preferably scalloped upwardly (that is, towards the upper rear strap 44 in the embodiments shown) to reduce interference of the lower edge of the headgear with the user's neck when the headgear is worn.

Figure 15:
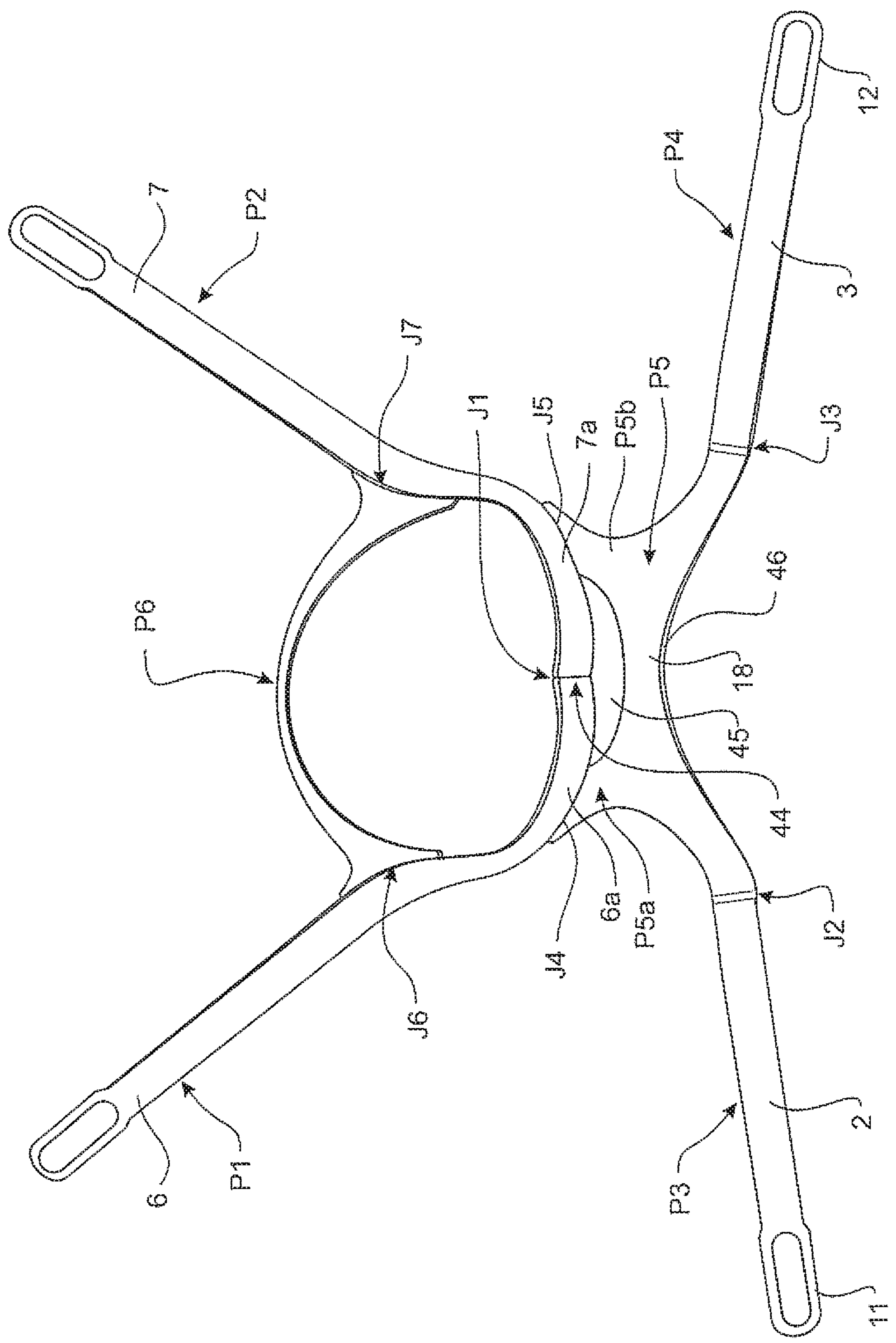
FIG. 15 shows the headgear of FIGS. 10 to 14 separated from the interface and laid out flat.
Figure 22:
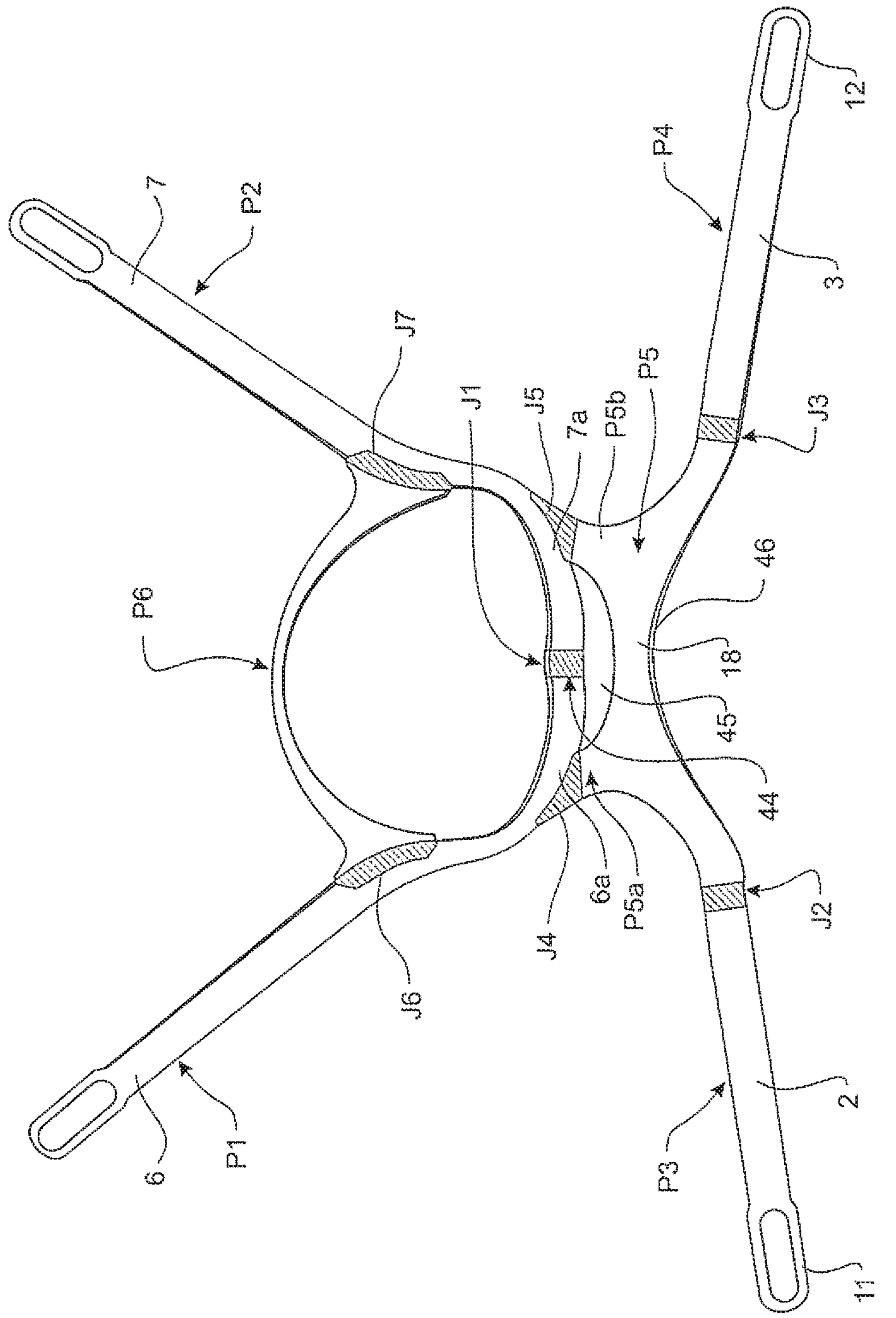
FIG. 22 shows the headgear of FIGS. 17 to 21 separated from the interface and laid out flat, showing the outside of the headgear.

The headgear may be formed by cutting from sheet material, such as by thermoforming (compressing under heat) an outline of the headgear shape in cloth covered foam sheet material such a BREATH-O-PRENE™ material for example, to define rounded edges in the subsequently cut out headgear, and then cutting out the headgear to shape from the sheet material, by blade or die cutting, laser cutting, or radio frequency cutting for example. Alternatively the headgear may be formed by joining together one or more separate sections of the same or different materials, which may be pre-cut and shaped material sections. For example one or more or each such section may be pre-cut by thermoforming an outline of the section shape in cloth covered foam sheet material to define rounded edges along at least some edges of the headgear section, and then cutting out the headgear section to shape. The sections are then joined to form the finished headgear and any joins may be formed by stitching or by ultrasonic or radio frequency welding, for example. One or more different sections may have different material properties such as different thickness, strength or stiffness, or extensibility for example, or be of different materials, from one or more other sections. Referring again particularly to FIGS. 15, 22, and 31 in the third, fourth, and sixth embodiments, and to FIG. 32 that shows a variation of the embodiment of FIG. 31, the headgear is formed by joining six separate sections of headgear material:

- two parts P1 and P2 which form the left and right upper straps 6 and 7, including curved rear portions 6*a* and 7*a*, and upper rear strap 44 of the rear part of the headgear—the parts P1 and P2 being joined at the rear of the headgear, centrally of upper rear strap 44 at joint 31;
- two parts P3 and P4 which form the left and right lower straps 2 and 3 and are joined to the lower rear of the headgear on left and right sides particularly to lower rear strap 18 on either side at left and right joins J2 and J3;
- part P5, preferably comprising a central portion with two substantially vertical portions and two side portions extending from the central portion, which comprises the lower rear strap 18 and is joined to the parts P1 and P2 at left and right joins 34 and 35, as well as to the parts P3 and P4 at joins J2 and J3 as stated above; and
- part P6 which comprises the top strap 9 and is joined to parts P1 and P2 at left and right joins J6 and J7. Join J7 is not shown in FIG. 31. It should be understood that end "A" of P6 is stitched, welded, or glued to P2 at a location on P2 mirroring the location of join J6 on P1, as shown in FIGS. 15 and 22. Forming join J7 creates a headgear that is contoured or three dimensional and cannot be laid flat in its entirety. In the embodiment of FIGS. 15 and 22, part P5 may have an approximate H-shape.

The width of the top strap part P6 may be wider at its ends which join the upper strap parts P1 and P2 than intermediate of the length of the top strap part P6 as shown. Similarly the width of segments P5*a* and P5*b* of the lower rear strap part P5 may have an extended width where these parts join to the parts P1 and P2 as shown. For example the top strap part P6 may be formed of a material having higher extensibility than other parts of the headgear, to provide a stretchable or relatively more stretchable crown strap for example.

Figure 31:
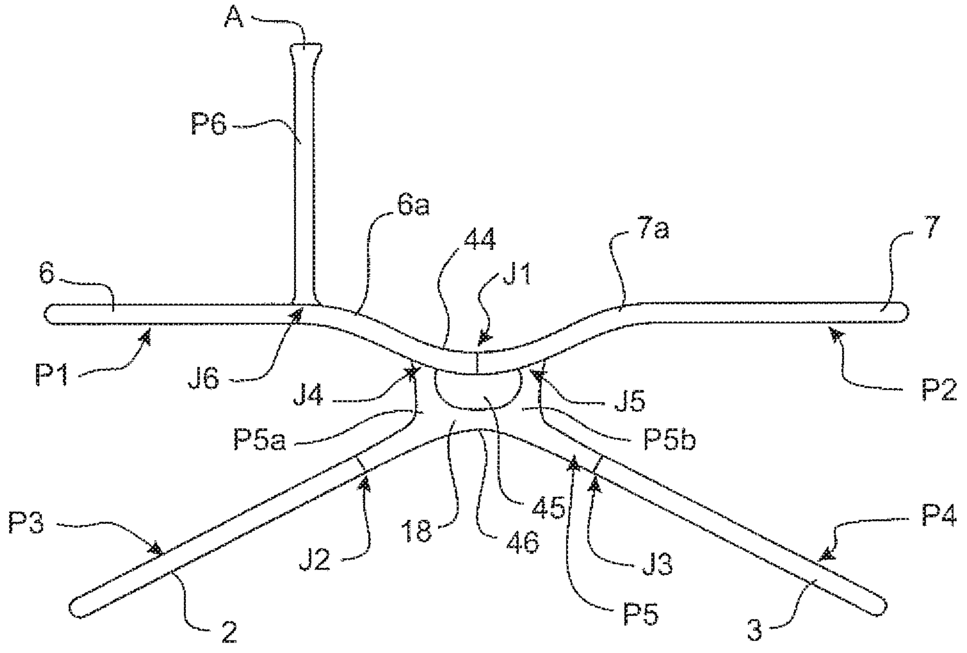
FIG. 31 shows the headgear of FIGS. 26 to 30 separated from the interface and laid out flat.
Figure 32:
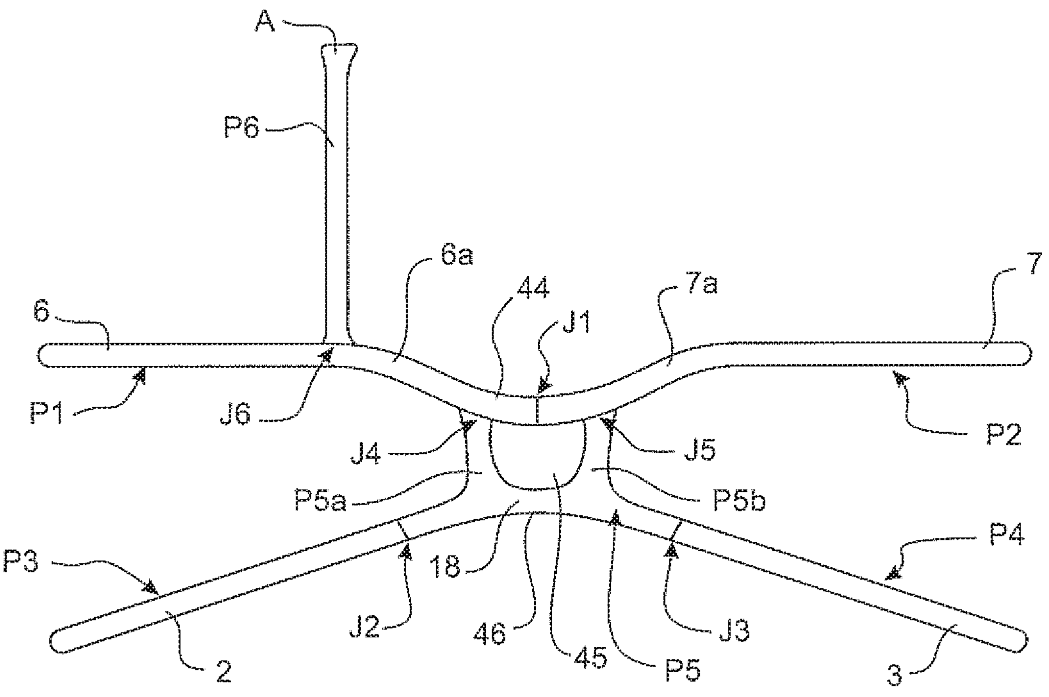
FIG. 32 shows an alternative embodiment of the headgear of FIGS. 26 to 30 separated from the interface and laid out flat.

Referring specifically to FIG. 32, it can be seen that the segments P5*a* and P5*b* are longer than the corresponding segments in FIG. 31, but are otherwise substantially vertical as in FIG. 31. Each of parts P3 and P4 extend from part P5 to define an angle relative to their corresponding part P1 or part P2 respectively that is less than the angle defined by those parts in FIG. 31.

Figure 33:
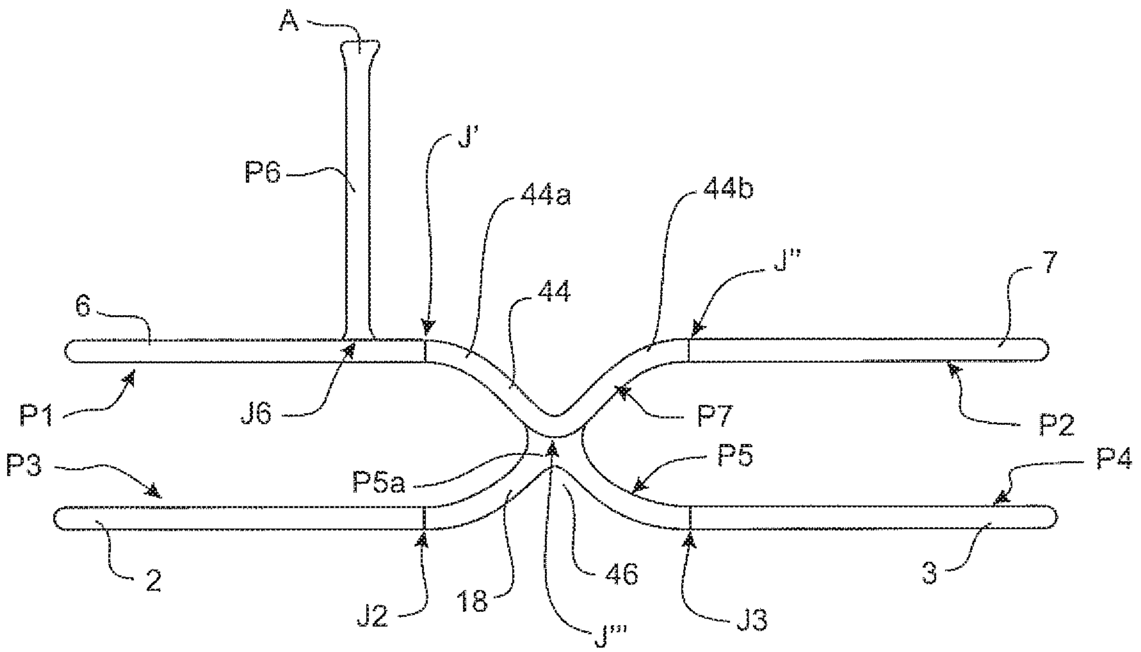
FIG. 33 shows a further alternative embodiment of the headgear of FIGS. 26 to 30 separated from the interface and laid out flat.

FIG. 33 shows an alternative embodiment to the headgear of FIGS. 31 and 32. The majority of the headgear is as described above in relation to FIGS. 31 and 32. However, parts P1 and P2 are joined to part P7 at left and right joins J' and J", parts P3 and P4 are joined to part P5 at left and right joins J2 and J3, and parts P5 and P5 are joined at join J'".

Referring again particularly to FIGS. 17 to 22, and 26 to 31 and 32, at one or more joins between any two headgear sections, the two headgear joined headgear sections may overlap and be joined through or at the overlap or area of overlap. That is, in manufacturing of the headgear, forming any such join may comprise positioning two (or more) headgear sections relative to one another such that they overlap at the join, and then for example radio frequency welding, or ultrasonic welding, or stitching, the two (or more) headgear sections together through or at the overlap. In FIGS. 17 to 22 of the fourth headgear embodiment all joins between the six separate sections of the headgear material are formed as such overlap joins, and by radio frequency welding of the two headgear sections together at each join. Specifically again:

- the two parts P1 and P2 which form the left and right upper straps 6 and 7, including curved rear portions 6*a* and 7*a*, and upper rear strap 44 of the rear part of the headgear, and are joined at the rear of the headgear, centrally of upper rear strap 44 at joint J1, are joined with an overlapped and radio frequency welded join;
- the two parts P3 and P4 which form the left and right lower straps 2 and 3 and are joined to the lower rear of the headgear on left and right sides particularly to lower rear strap 18 on either side are joined with overlapped and radio frequency welded left and right joins J2 and J3;
- the part P5, preferably comprising a central portion with two substantially vertical portions and two side portions extending from the central portion, which comprises the lower rear strap 18 is joined with overlapped and radio frequency welded left and right joins J4 and J5 to the parts P1 and, as well as to the parts P3 and P4 at joins J2 and J3 as stated above; and
- the part P6 which comprises the top strap 9 and is joined to parts P1 and P2 at overlapped and radio frequency welded left and right joins J6 and J7. Join J7 is not shown in FIG. 31. It should be understood that end "A" of P6 is overlapped and radio frequency welded to part P2 at a location on P2 mirroring the location of join J6 on P1, as shown in FIGS. 15 and 22. Forming join J7 creates a headgear that is contoured or three dimensional and cannot be laid flat in its entirety.

Referring to FIGS. 15, 22, 23, and 31 to 33, with or without the sections of high friction material of FIG. 24 (described below), joins 32 and 33 are preferably located so that in use the joins will sit below and/or behind each ear of the user.

The headgear may be formed to have different levels of resilient extensibility or stretchability (hereinafter generally referred to as stretchability) in different parts or straps of the headgear. One or more different sections of material from which the headgear is formed may have different stretchability than one or more other headgear sections, such as higher or lower stretchability. The headgear may be formed to have four (or more) different levels of stretchability in four or more different parts or straps of the headgear. Four (or more) different sections of material from which the headgear is formed may have four (or more) different stretchability.

Referring again particularly to FIGS. 17 to 22, and 26 to 31 and 32, the headgear of these fourth and sixth embodiments is formed to have four different levels of resilient extensibility or stretchability in different parts or straps of the headgear. The headgear is formed from four materials each having a different level of stretchability. In the embodiment shown top strap 9 has the highest relative stretchability. The rear part of the headgear comprising lower rear strap 18 has a next or second highest relative stretchability (relative to the top strap 9). The left and right upper straps 6 and 7 and upper rear strap 44 have a relatively lower or third highest stretchability, i.e. lower than the than lower rear strap 18. The left and right lower side straps 2 and 3 which when the headgear is worn extend from a rear part 4 of the headgear along the left and right sides of the users head below the ears to connect to the interface have the lowest stretchability, and may be substantially inextensible or non-stretch.

Thus and referring again particularly to FIGS. 22, 31 and 32:

- the part P6 which comprises the top strap 9 is formed of a first material having highest stretch;
- the part P5, preferably comprising a central portion with two substantially vertical portions and two side portions extending from the central portion, which comprises the lower rear strap 18 is formed of a second material having next highest or a first intermediate stretch;
- the two parts P1 and P2 which form the left and right upper straps 6 and 7 are formed of a third material having a lower again or second intermediate stretch; and
- the two parts P3 and P4 which form the left and right lower straps 2 and 3 are formed of a fourth material having lowest extensibility or stretch or which may be substantially non-stretch.

In another embodiment, and referring again particularly to FIGS. 22, 31 and 32:

- the part P6 which comprises the top strap 9 is formed of a first material having highest stretch;
- the two parts P1 and P2 which form the left and right upper straps 6 and 7 are formed of a second material having the next highest or a first intermediate stretch;
- the part P5, preferably comprising a central portion with two substantially vertical portions and two side portions extending from the central portion, which comprises the lower rear strap 18 is formed of a third material having a substantially similar stretch to parts P1 and P2, or a lower again or second intermediate stretch; and
- the two parts P3 and P4 which form the left and right lower straps 2 and 3 are formed of a fourth material having lowest extensibility or stretch or which may be substantially non-stretch.

Again referring to FIGS. 15, 22, 23, and 31 to 33, with or without the sections of high friction material of FIG. 24 (described below), joins 32 and 33 are preferably located so that in use the joins will sit below and/or behind each ear of the user, as described above. In embodiments where the lower side straps formed by parts P3 and P4 are of the lowest extensibility or stretch or which are substantially non-stretch, the location of joins J2 and 33 below and/or behind each ear of the user allows the lower rear strap 18 of the rear part of the headgear to grip the user's head and retain the headgear and respiratory interface in place, such as against the blow-off force created by the CPAP, and/or against forces applied to the mask by a user's movement during sleep.

In any embodiment described herein, the materials may be different materials such as materials of different composition of materials of similar composition but different thicknesses, to achieve different stretchabilities, or may be the same or similar materials which are given different stretchability by for example being perforated or otherwise manufactured to increase stretchability. For example the headgear sections of higher stretchability may be perforated to increase their stretchability over the equivalent non-perforated material. Headgear sections of intermediate stretchability may be less densely perforated to increase their stretchability over the equivalent non-perforated material but less so than more highly perforated sections. Headgear sections of low or no stretchability may be non-perforated or may be surface coated, or comprise a non-stretch or low-stretch outer fabric layer, or be otherwise treated, to reduce any inherent stretchability. Headgear sections of low or no stretchability may be formed from a material having an internal non-stretch or limited-stretch layer, such as a plastic film layer, between one or more outer layers on one or both sides, which may be higher stretch and may be foam and/or fabric layers.

Instead of being formed of separate sections of material as described above with reference to FIGS. 10 to 22 the headgear may be formed by cutting all of the headgear from a single section of material and then perforating different parts of the headgear to give these parts the desired levels of different stretchability. For example the rear strap(s) 18 and top strap 9 may be most highly perforated, and the upper straps 6 and 7 may be less densely perforated. Optionally one or more parts such as lower straps 2 and 3 may be non-perforated to be least stretchable, or surface coated or otherwise treated to reduce any inherent stretchability.

In the fourth and sixth embodiments described above the lower rear strap 18 is relatively highly stretchable so that it provides a stretchable segment in the 'lower loop' defined by the mask, the lower side straps 2 and 3, and the lower rear part 18 of the headgear, which enables this part of the headgear to open up when pulled by a user over the head when donning the headgear (and the same when removing the headgear). This may enable a user to don the headgear without first loosening or opening the headgear, i.e. the user leaves the straps 2 and 3 fixed back upon themselves in the position of last wearing of the headgear, instead of first releasing the straps so that the while donning the headgear the hardstops are against the frame as described above, and instead simply pulls the headgear down over the user's head, the stretchable rear of the headgear stretching as needed as the user does so. At the same time the lower side straps 2 and 3 are relatively low stretch or no stretch to reduce discomfort due to these straps stretching and contracting against the wearer's face as the user moves, when the headgear is worn. Low or no stretch lower side straps 2 and 3 may reduce leakage between the seal of the interface and the wearer's face due to pressure variations within the mask as the wearer breathes in and out against air pressure, in a CPAP application for example. The 'upper loop' comprising the upper side straps 6 and 7, and the upper rear part 44 of the headgear is less stretchable than the most stretchable top strap 9 so that both the top strap 9 and this upper loop around the top of the head can accommodate different head sizes, but the upper loop straps grip around the head sufficiently to prevent the return or elastic resiliency of the top strap 9 pulling the upper loop higher on the wearer's head than intended. That is, when a wearer dons and adjusts the position of the headgear on the wearer's head, the grip of the upper loop on the head is sufficient to maintain the upper loop (and thus the whole headgear) In place where it is initially located by the wearer, against any upward elastic pulling force provided by the top strap 9. Also to assist, the inside of the upper loop parts of the headgear may be formed of a relatively high friction material for example. Furthermore, the stretch of the upper loop and/or the upper side straps allows a user to adjust the position of the forehead support for comfort.

Figure 23:
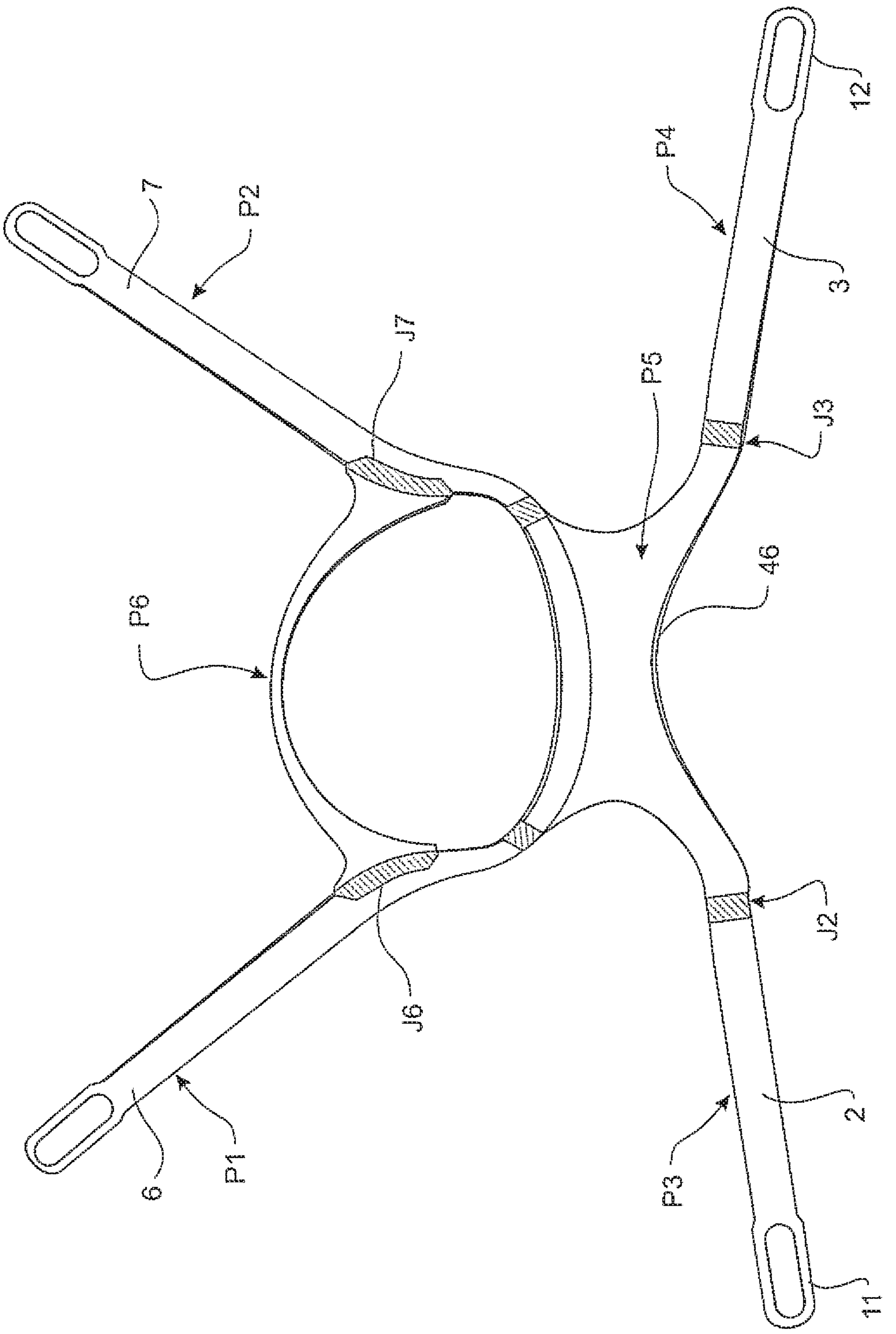
FIG. 23 is a view similar to FIG. 22 but of headgear of a fifth embodiment of the invention.

FIG. 23 is a view similar to FIG. 22 but of headgear of a fifth embodiment of the invention which is similar to that of FIGS. 17 to 22 but in which the rear part 4 of the headgear comprises a single or one piece rear part 4 as shown (the rear part 4 does not comprise upper and lower rear straps with an opening between). The rear part may have similar stretch to that of the top strap 9, or less stretch than the top strap 9, and either more or the same as the upper side straps 6 and 7. The one piece rear part 4 may be thicker than other parts of the headgear to provide structure and shape to the headgear, and optionally at the same time may be perforated or otherwise manufactured to have the desired stretch characteristics, such as high stretch for example higher stretch than other parts of the headgear but lower stretch than the top strap 9.

In another embodiment, and referring again particularly to FIGS. 22, 31 and 32:

- the two parts P1 and P2 which form the left and right upper straps 6 and 7 are formed of a first foam material having a first density;
- the part P6 which comprises the top strap 9 is formed of a second foam material having a second density that is lower than the first density;
- the part P5, preferably comprising a central portion with two substantially vertical portions and two side portions extending from the central portion, which comprises the lower rear strap 18 is formed of a third foam material having a substantially similar density to part P6 but having a thickness that is greater than the thickness of part P6, including a thickness that is at least about 10%, 25%, 50%, 75%, or 100%, or more greater than the thickness of part P6; and
- the two parts P3 and P4 which form the left and right lower straps 2 and 3 are formed of a fourth foam material that has a lower extensibility or stretch than the first, second, or third materials, or which may be substantially non-stretch.

In this embodiment, the resulting foam material density and thickness leads to

- the part P6 which comprises the top strap 9 having highest stretch;
- the two parts P1 and P2 which form the left and right upper straps 6 and 7 having the next highest or a first intermediate stretch;
- the part P5 which comprises the lower rear strap 18 having a substantially similar stretch to parts P1 and P2, or a lower again or second intermediate stretch; and
- the two parts P3 and P4 which form the left and right lower straps 2 and 3 having lowest extensibility or stretch or which may be substantially non-stretch.

In such embodiments, the part P5 of the headgear maintains separation between the upper and lower straps and/or structure or 'as worn' shape to the headgear. For example, and referring to FIGS. 2 and 3, a headgear of this embodiment omits structure element 21 and instead the structure of part 5 acts so that the headgear maintains separation between the upper and lower straps and/or structure or 'as worn' shape when not worn, i.e. before being donned, The headgear structure may be such that the headgear does not lie without structure or shape when not worn but instead maintains a three dimensional structure or shape approximately similar to that of the headgear when worn. This may indicate to a user how the headgear is to be worn. The headgear may be formed to adopt this structure or shape when initially removed from its packaging (or from storage)—that is, if the headgear is constrained to a flatter or other shape when packaged, then memory built into the part P5 for this shape causes the headgear to adopt this shape when removed from the constraints of the package (so that it is apparent to the user how the headgear is to be worn).

Figure 17:
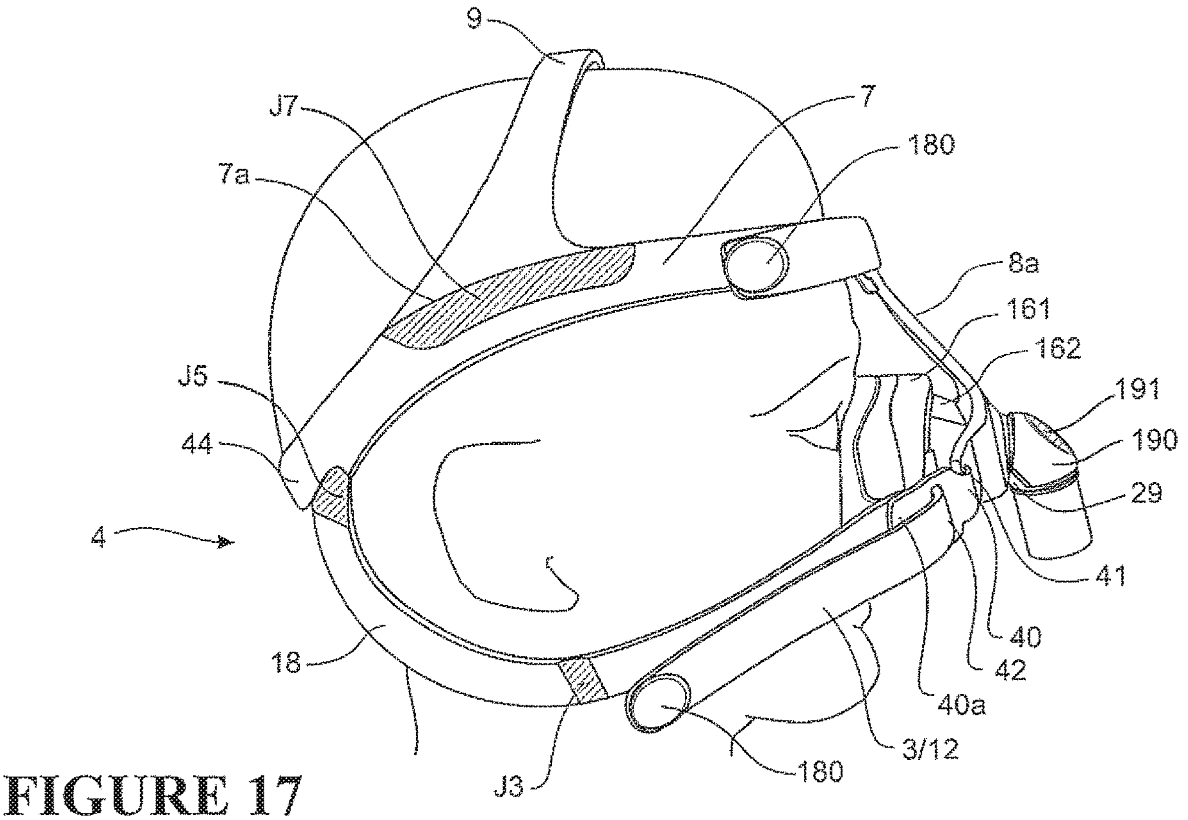
FIG. 17 is a right side view of a fourth embodiment of headgear of the invention, and an (indirect) nasal interface, worn by a user.
Figure 18:
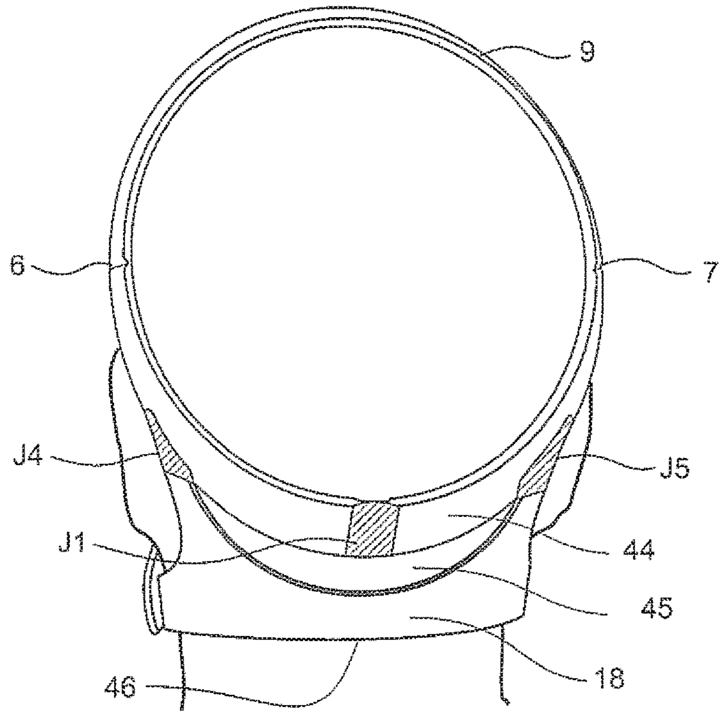
FIG. 18 is a rear view of the headgear of and interface of FIG. 11, worn by a user.
Figure 24:
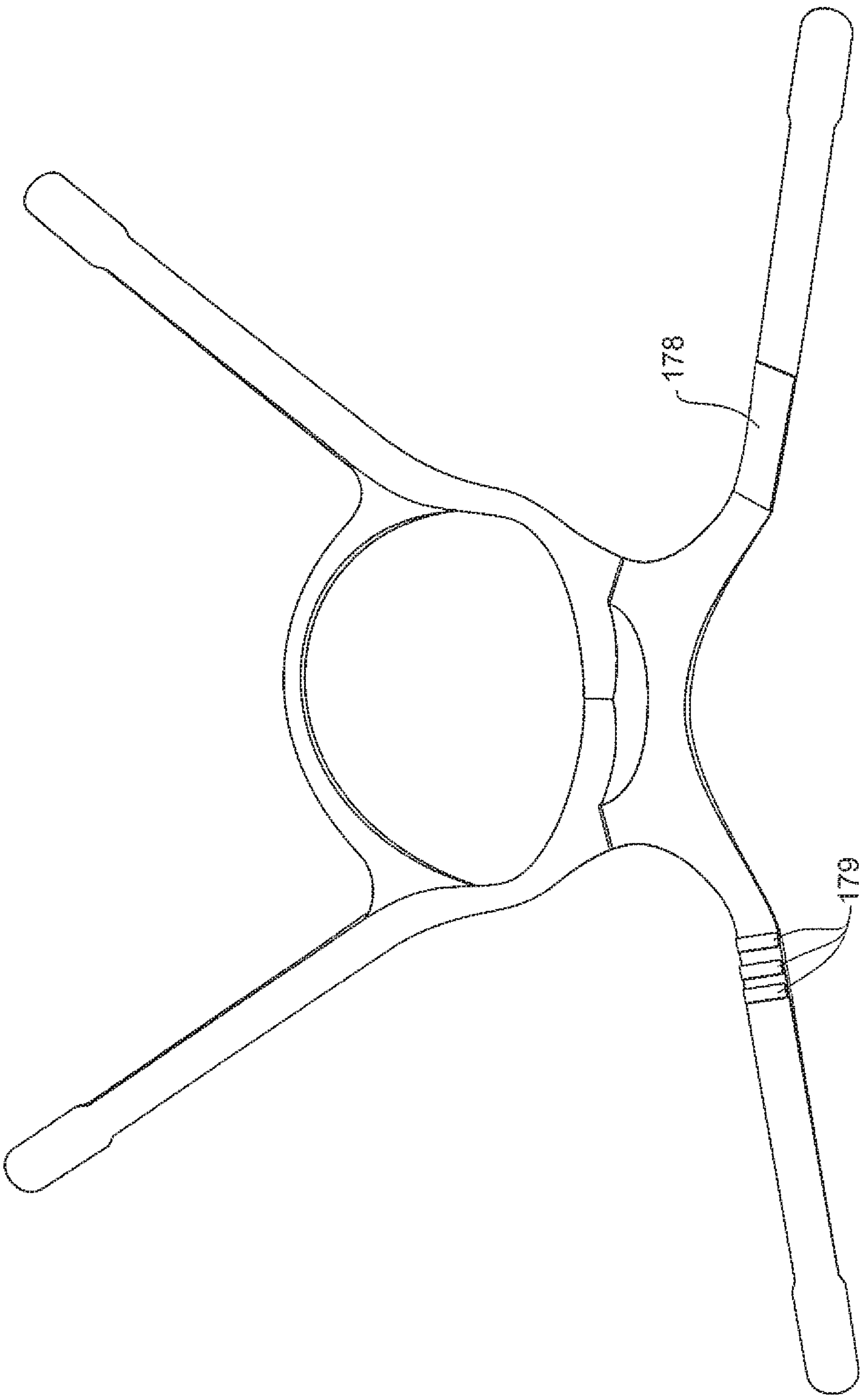
FIG. 24 shows the headgear of FIGS. 17 to 21 separated from the interface and laid out flat similar to FIG. 22 but showing the inside of the headgear.

FIG. 24 shows the headgear of FIGS. 17 to 21 separated from the interface and laid out flat similar to FIG. 22 but showing the inside of the headgear. As shown in this figure, lower rear parts of the headgear may comprise sections 178 and 179 of high friction material which when the headgear is worn are located below or towards the bottom of the ears and behind the ears but not as far back as the back of the neck, and which will assist in inhibiting the lower side straps 2 and 3 from riding up (rising vertically) when the headgear is worn, particularly when a wearer temporarily lifts the mask off the face without releasing the headgear, i.e. while the headgear is under some tension, to adjust the position of the mask on the wearer's face. Adjusting the mask position in this way, for example, can cause the lower side straps to ride up either causing discomfort against the ears or requiring further headgear adjustment. Such sections of high friction material may also act to reduce or prevent horizontal forwards movement of the headgear resulting from the blow-off force created by the CPAP, and resulting from changes in the blow-off force during periods of use that result from CPAP therapy pressure changes. If the headgear moves forward too much, the seal between the patient interface and the user will become less engaged and leaks may result. In FIG. 17 which shows the headgear worn, and a high friction section may be located at J3, as indicated in phantom outline. Such high friction sections may be positioned to overlay the lower occipital bone when the headgear is worn and/or or the neck behind the jaw and/or between the lower occipital bone and the neck behind the jaw. They may be integral in the headgear or attached to the inside surface of the headgear or printed on the inside surface of the headgear, for example. Such high friction sections may comprise a single relatively larger section or area 178 or multiple adjacent but separated sections or areas 179.

Figure 25A:
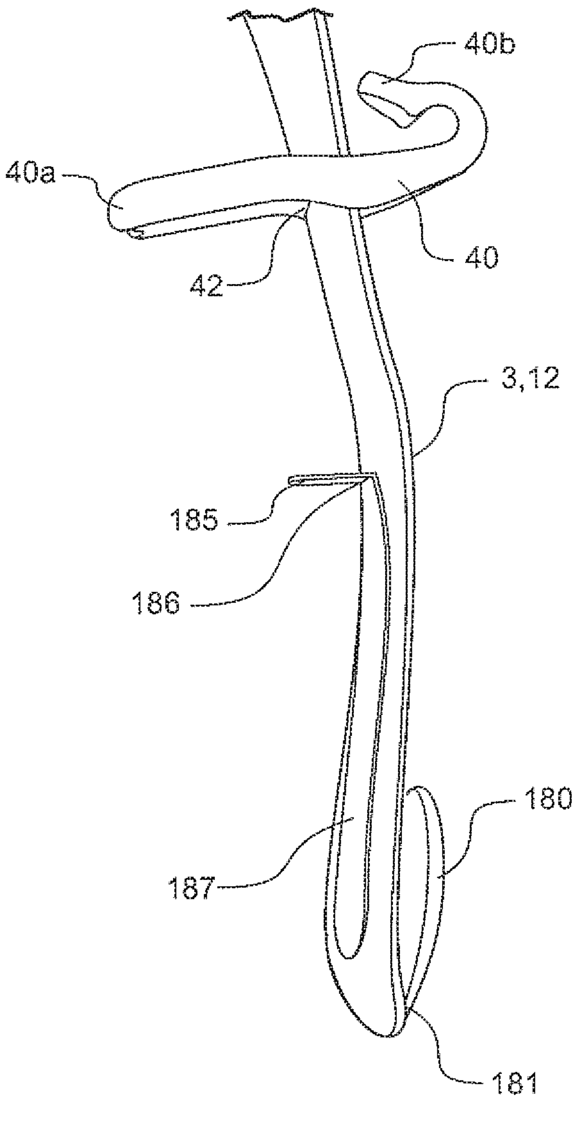
FIGS. 25A and 25B are enlarged views of the end of a right lower strap of the headgear of FIGS. 17 to 22.
Figure 25B:
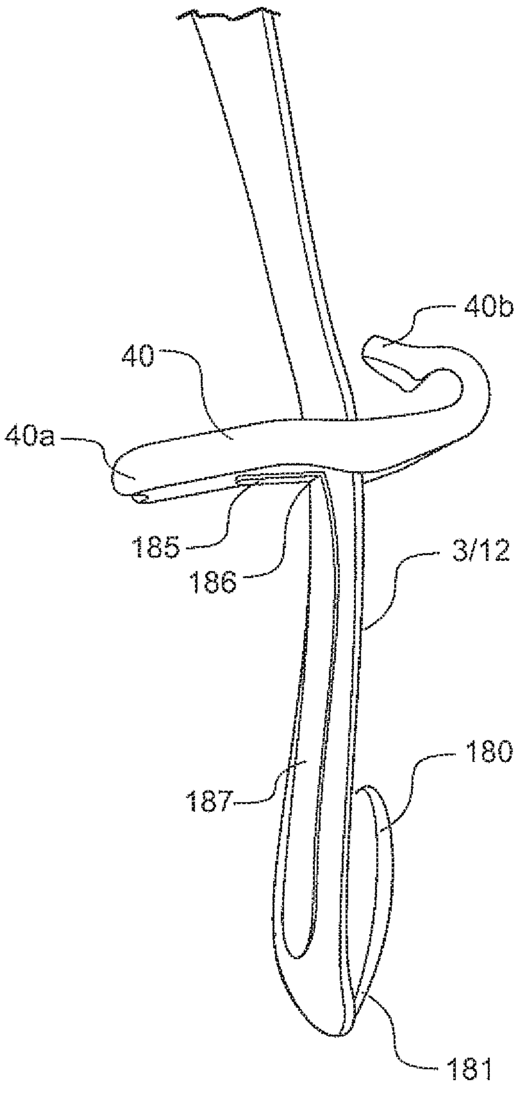
Figure 26:
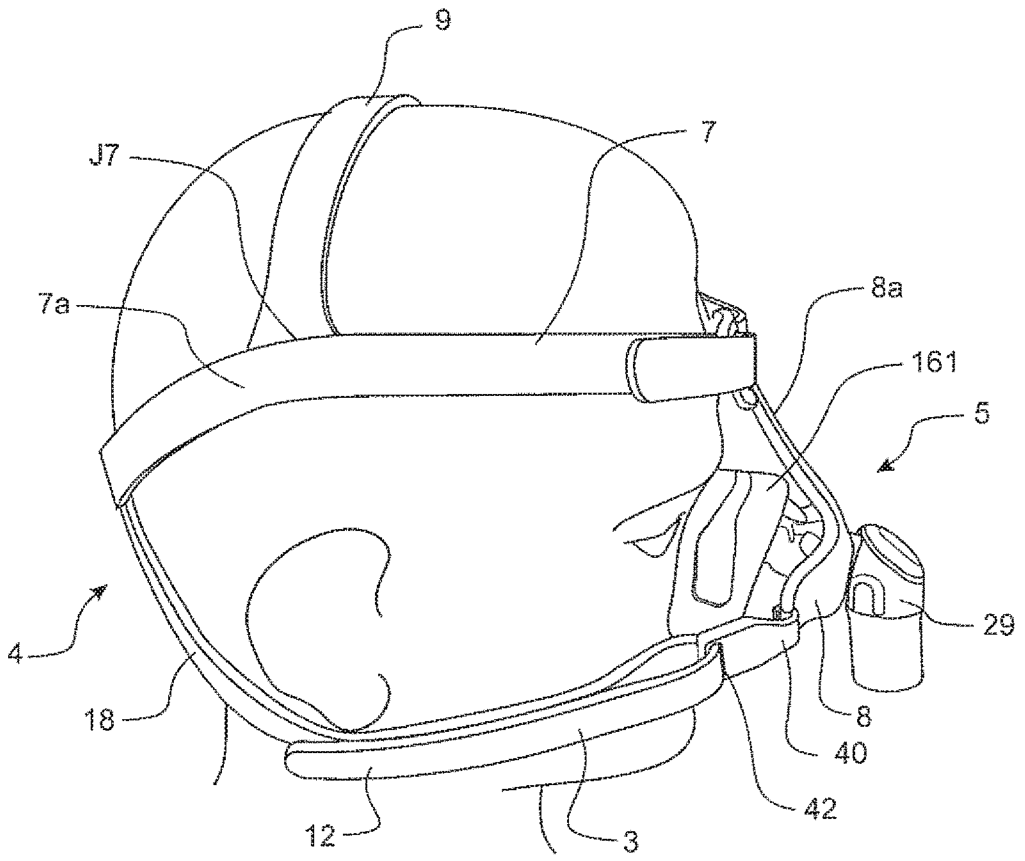
FIG. 26 is a right side view of a sixth embodiment of headgear of the invention, and an (indirect) nasal interface, worn by a user.
Figure 27:
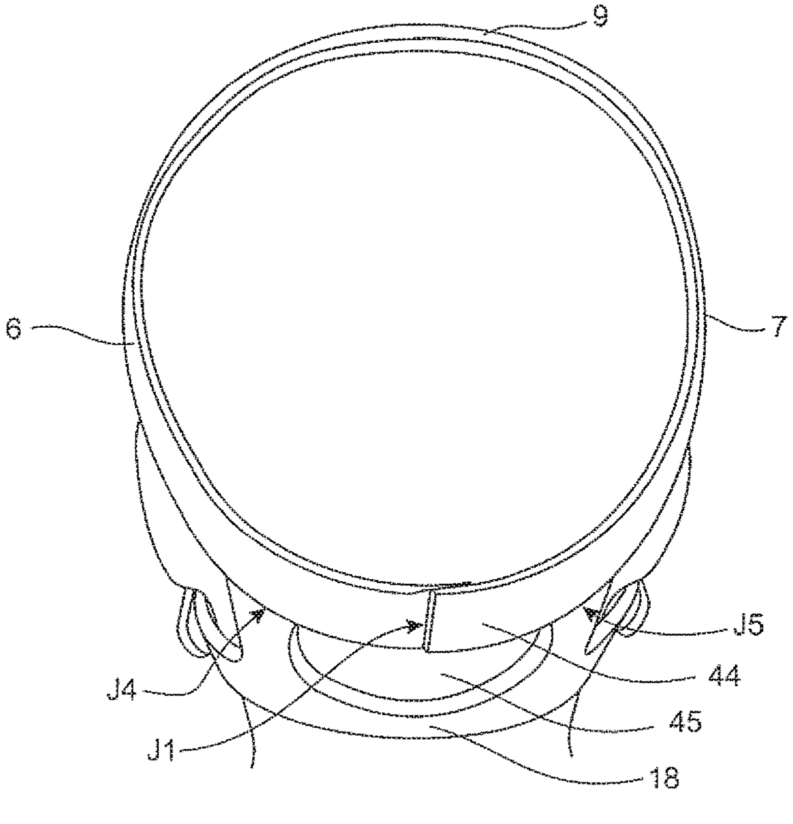
FIG. 27 is a rear view of the headgear of and interface of FIG. 26, worn by a user.
Figure 28:
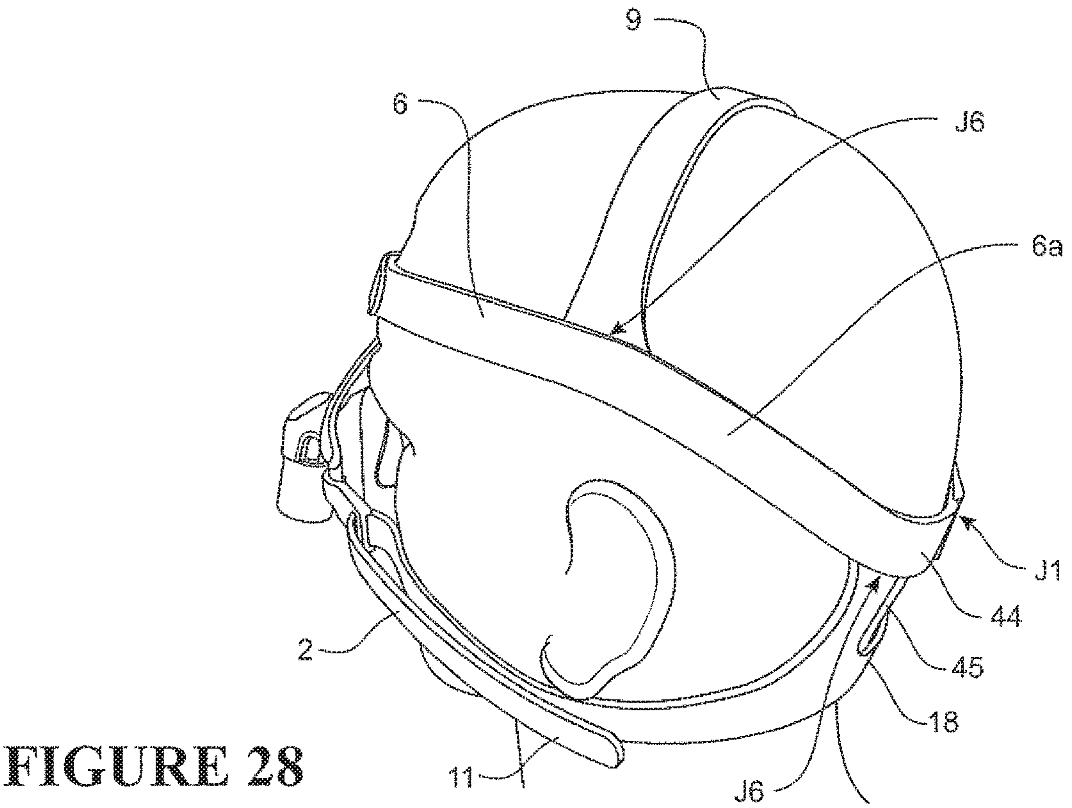
FIG. 28 is a three quarter view from the left rear of the headgear of and interface of FIGS. 26 and 27, worn by a user.

FIGS. 25A and 25B are enlarged views of the end of a right lower strap of the headgear of FIGS. 17 to 22. Such straps may be used in any embodiment described herein, including the sixth embodiment of FIGS. 26 to 31, and the embodiments of FIGS. 32 and 33, and for upper side straps of any embodiment described herein. The distal end of the strap passes through a slot-shaped opening 42 in the hook connector 40 as described previously. Alternatively the ends of the lower straps pass through slot-shaped openings on left and right sides of the mask frame. In the embodiment shown the far end of the strap beyond the near end comprises a flexible tab 180. This tab 180 is on an outside of the strap end ('outside' when the strap is not doubled back on itself and the strap end fixed down). The tab is attached to the headgear at 181. The tab is flexible and may optionally be formed from a similar material to the main body of the headgear such as a foam and fabric material, and provides a grip tab which a wearer may grasp to lift the strap end to readjust the headgear, or before doffing the head gear. The tab 180 also inhibits the end of the strap being pulled out of the slot 42 in hook 40.

In the embodiment shown the near end also comprises a flexible tab 185. This tab 185 is on an inside of the strap end ('inside' when the strap is doubled back on itself and the strap end fixed down). The tab 185 is attached to the headgear at 186. The tab 185 is an extension of plastic backing material of a hook (of hook and loop) fastening panel 187 of the strap end. Thus the tab 185 may be less flexible but is effectively hingedly mounted to the strap, with some memory towards the position shown in FIG. 25A so that when the strap is not doubled back on itself and the strap end fixed down, it will tend to adopt the position shown. The tab 185 thus also inhibits the end of the strap being pulled out of the slot 42 in hook 40, as shown in FIG. 25B.

Either or both of such tabs 180 or 185 may be provided on any one or more strap ends, of upper or lower side straps, of any headgear embodiment described herein. For example as shown in FIGS. 17-22 tabs 180 are provided on all strap ends. Tabs 185 are provided only on lower strap ends.

The tabstops may be a contrasting color to the rest of the headgear.

Hook connector 40 comprises tab 40*a* and hook portion 40*b*. Tab 40*a* is an elongate rear section of hook connector 40 that provides gripping surfaces. Portion 40*b* is preferably shaped to provide a wide angle of engagement with corresponding slots on frame 8. As described above, end portions of straps used herein comprise a section of hook material which may attach to a fabric surface layer of the straps at least on the operator side, intermediate of the strap length, to fix the strap ends when the straps are tightened, or alternatively a matching section of loop material may be provided on the strap. In use, an end portion of a strap, such as a strap 2, 3, 6, 7 described above, is folded back on and affixed to itself, forming a loop of strap holding hook connector 40, as shown in FIG. 17. Tab 40*a* will lie between the folded sections of strap and can be gripped, together with the folded strap, to removably attach hook portion 40*b* to, for example, slot-shaped openings 13,41 in frame 8 of the embodiments described above, or in similar slots in forehead rest 8*a* (not shown). This arrangement with lower side straps is shown in use in FIG. 17.

The mask with which headgear as described above in all embodiments may comprise an indirect or direct nasal including nozzles, pillows, or cannula, oral, or full face interface. In the third embodiment, of FIGS. 10 to 16 the interface is a full face interface (which covers the nose and mouth). In the fourth and sixth embodiments, of FIGS. 17 to 22 and 26 to 31 respectively, the interface is an indirect nasal interface (which covers the nose only).

Figure 35:
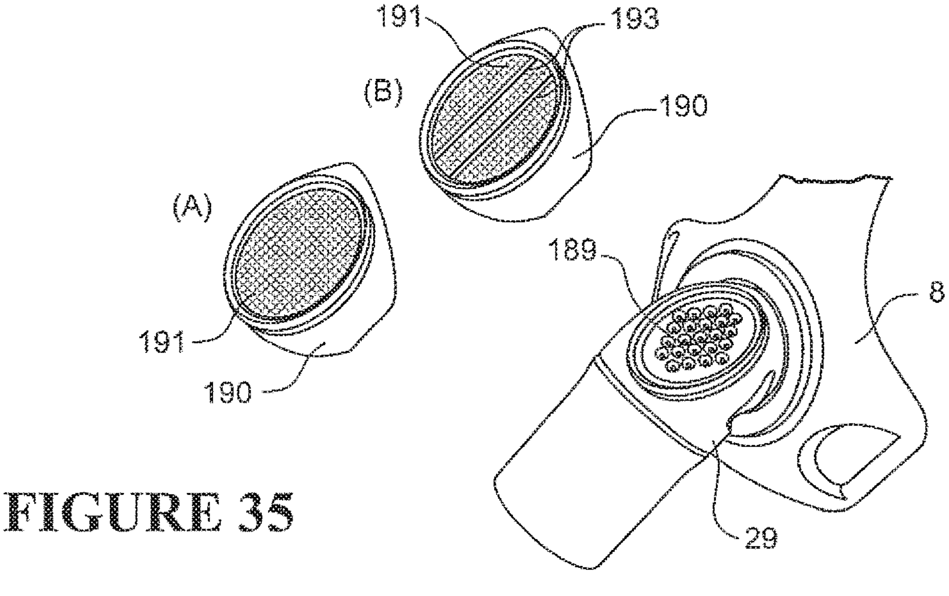
FIG. 35 shows further detail of the elbow of FIGS. 17 to 21 and 26 to 31.

The interface may comprise an elbow 29 connected to an opening through the frame 8. The elbow may be a swivelling elbow. In preferred forms the connection of the elbow to the frame provides for both rotation and pivoting of the elbow relative to the frame. For example the connection may comprise a ball joint connection to the frame so that the elbow can pivot about axes parallel to and perpendicular to its connection with the mask. The elbow is connected to the end of a length of flexible tubing (not shown). The other end of tubing terminates with a connector. The elbow may include a gas washout vent or vents. In the embodiments of FIGS. 17 to 21 and 26 to 31, and as shown in detail in FIG. 35 the elbow includes gas washout vents 189 through the elbow 29 to the exterior and also a diffuser of a non-woven material, for noise reduction, over the washout vents on the exterior of the elbow. The diffuser material 191 is mounted in a cap 190 which is a snap fit onto the exterior of the elbow 29 or otherwise attaches to the elbow, over the gas washout vents 189. The cap 190 may be of a plastics material overmoulded around the peripheral edges of the diffuser material to capture the edges of diffuser material in the plastic moulded cap and form a one piece component. Alternatively the peripheral edges of the diffuser material may be bonded to the plastic moulded cap, by plastic welding for example, to form a one piece component. The cap 190 may include a grill 193, as shown in FIG. 35B. Alternatively gas washout vent(s) may be provided on the frame for example.

Figure 13:
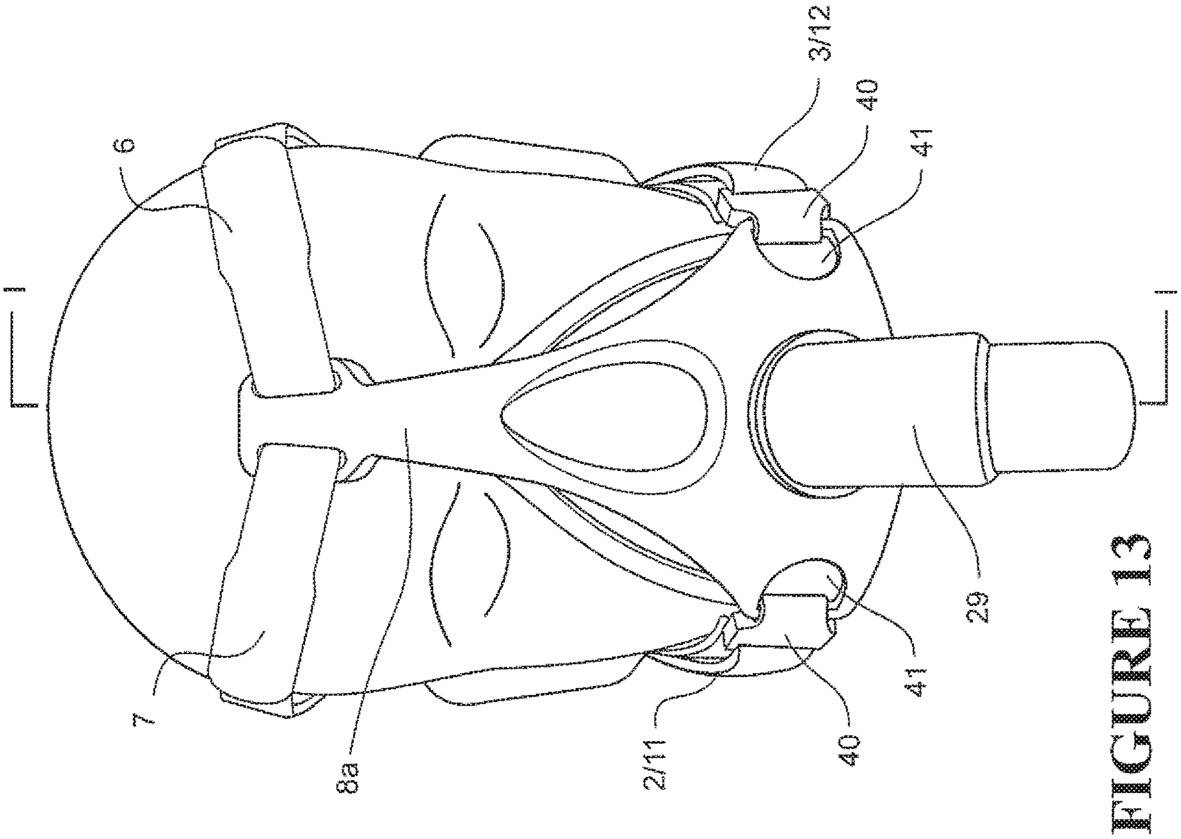
FIG. 13 is a front view of the headgear of and interface of FIGS. 10 to 12, worn by a user.
Figure 12:
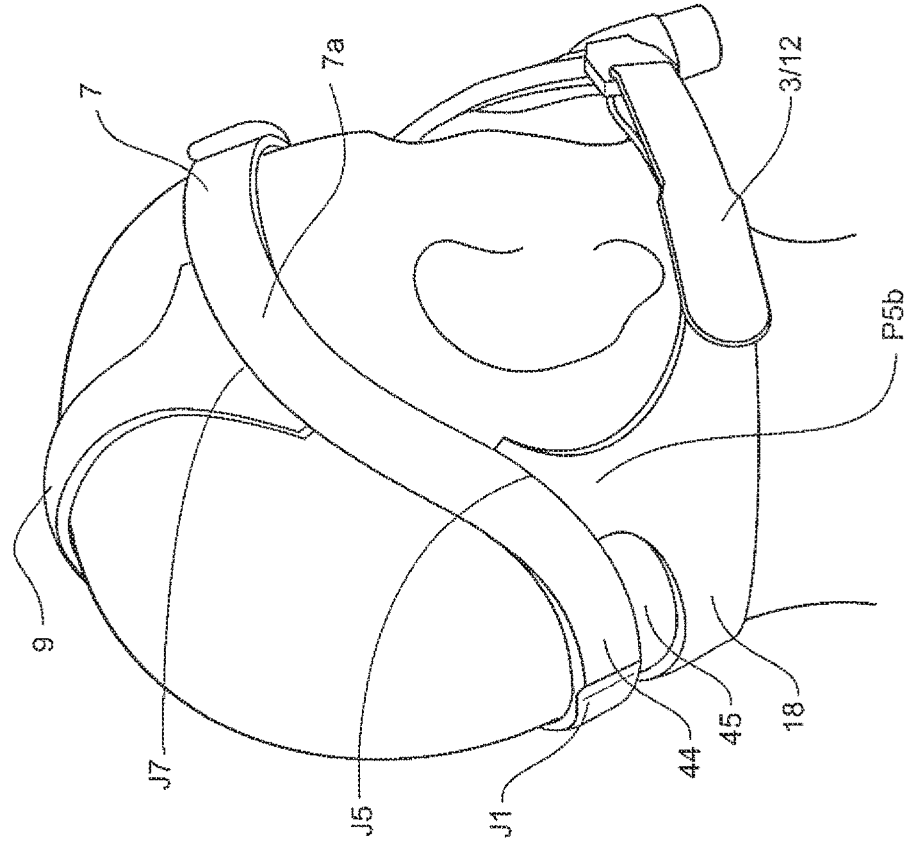
FIG. 12 is a three quarter view from the right rear of the headgear of and interface of FIGS. 10 and 11, worn by a user.
Figure 14:
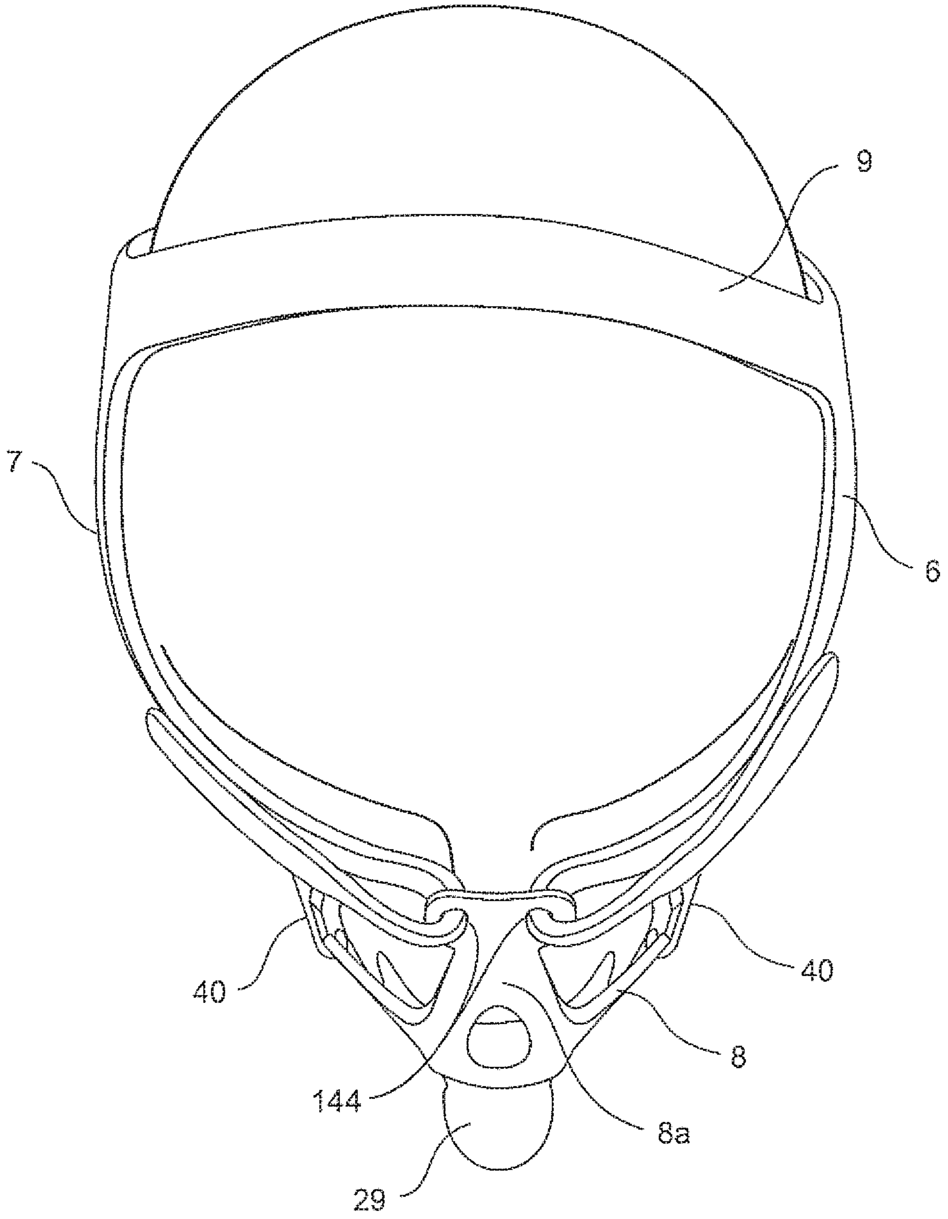
FIG. 14 is a view from above of the headgear of and interface of FIGS. 10 to 13, worn by a user.
Figure 16:
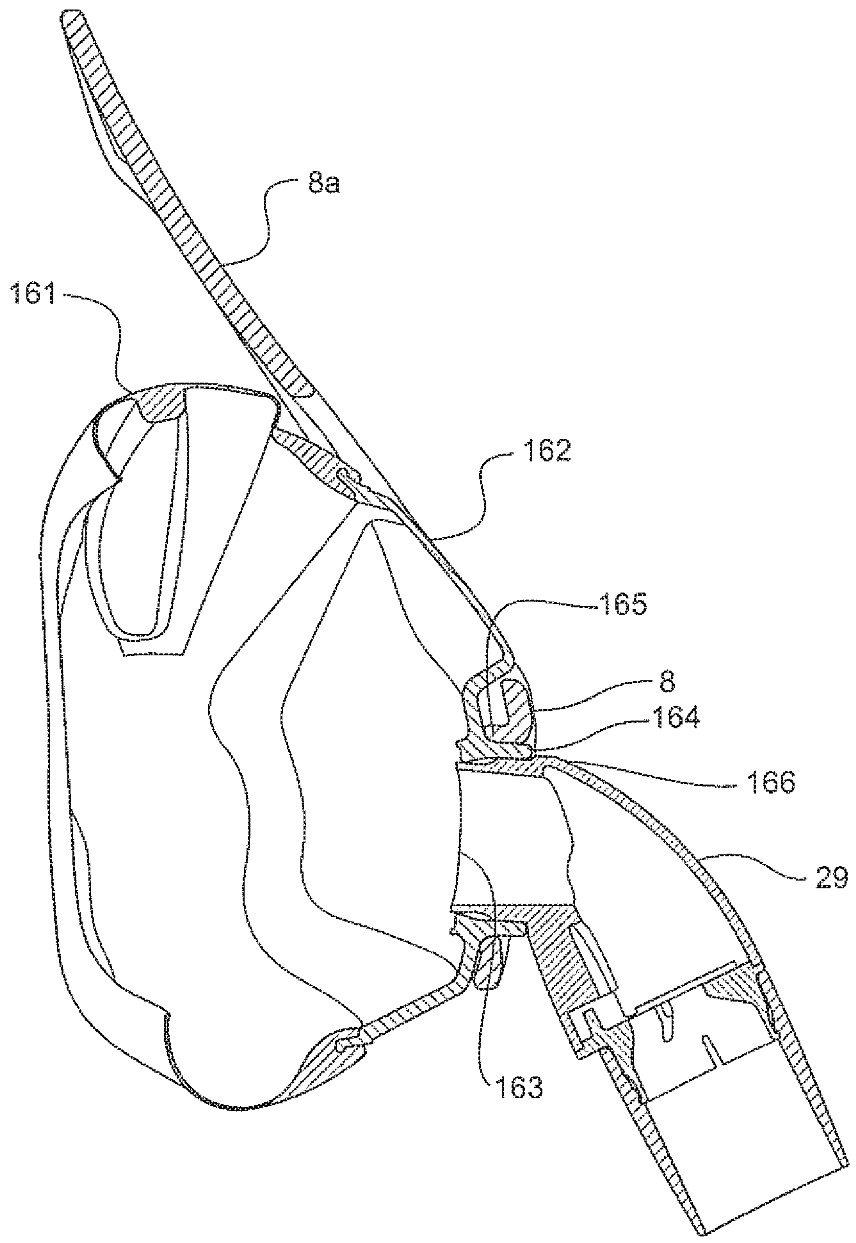
FIG. 16 is a cross-section view along line I-I of FIG. 13, of the shell and seal, elbow, and frame, of the mask of the embodiment of FIGS. 10 to 15.

FIG. 16 is a cross-section view along line I-I of FIG. 13, of the shell and seal, elbow, and frame, of the full face interface of the third embodiment of FIGS. 10 to 15. In the embodiment shown the interface comprises seal-shell, frame, and elbow components. The soft seal 161, which may be for example a single or double flap or lip seal formed of a silicone material, is fixed to shell component 162 (to form a seal-shell component). Optionally the indirect nasal interface of the fourth embodiment may comprise a similar seal and/or seal-shell structure. Referring still to the third embodiment as shown in FIG. 16, the shell 162 comprises a gases entry opening 163 with therearound an outwardly (or alternatively inwardly) projecting annular collar 164. The upper annular end 166 of the elbow 29 fixes into the internal diameter of this collar 164, for example in a click or snap fit, when the mask is assembled for use, so that the elbow is coupled to the shell 162 (rather than to the frame). The shell 162 in turn couples to the frame by the collar 164 being received in the aperture in the frame, which preferably comprises a surrounding annular collar 165 into which the external diameter of the shell collar 164 is received in a click or snap fit. Alternatively the seal-shell component may comprise a single material seal component.

Figure 20:
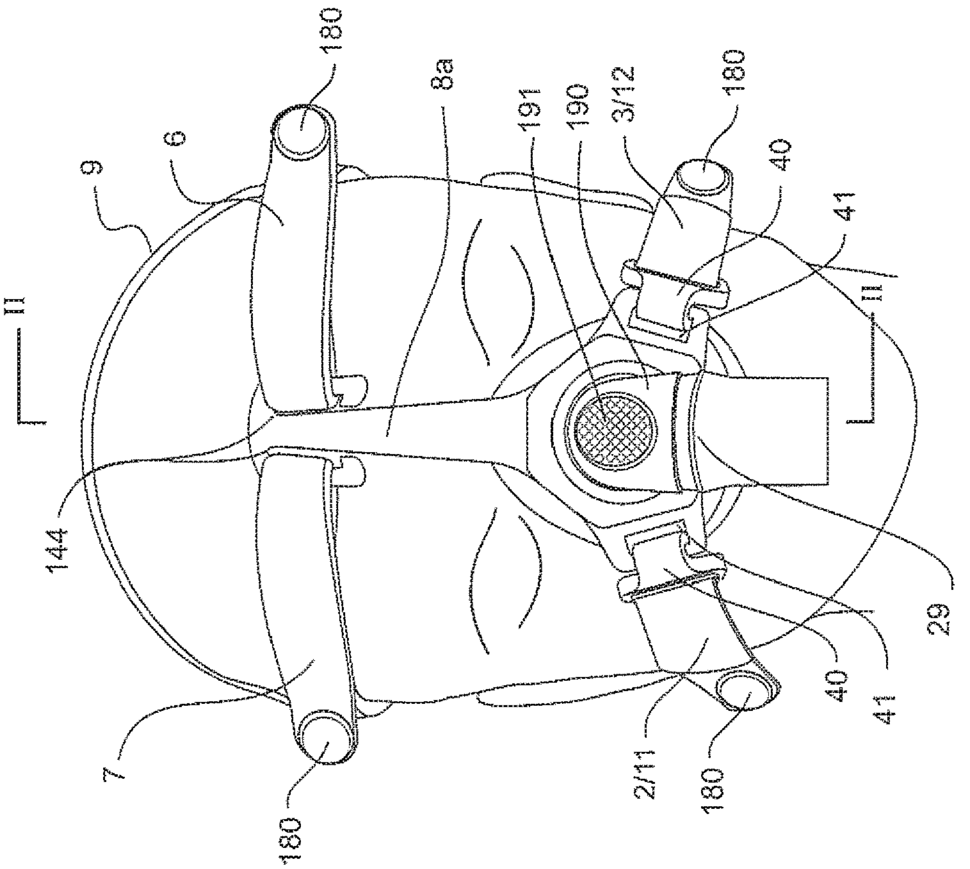
FIG. 20 is a front view of the headgear of and interface of FIGS. 17 to 19, worn by a user.
Figure 19:
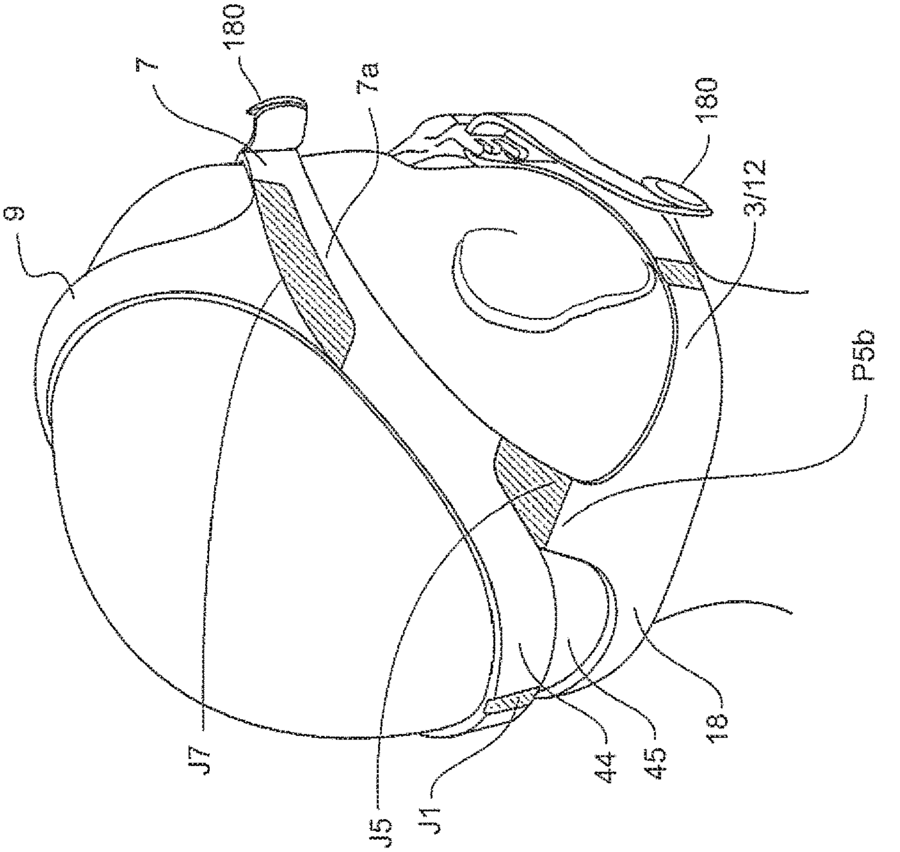
FIG. 19 is a three quarter view from the right rear of the headgear of and interface of FIGS. 17 and 18, worn by a user.
Figure 21:
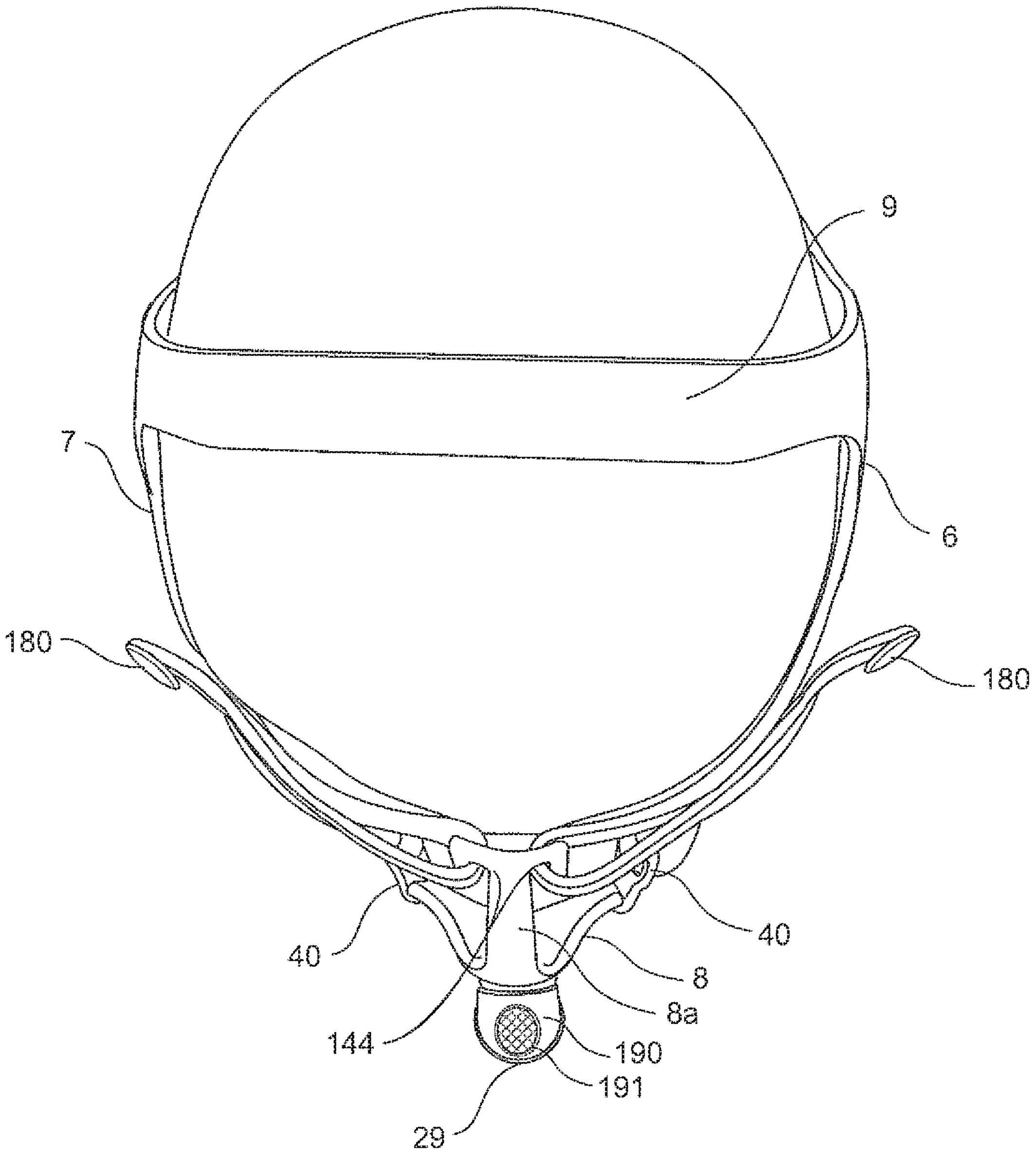
FIG. 21 is a view from above of the headgear of and interface of FIGS. 17 to 20, worn by a user.
Figure 29:
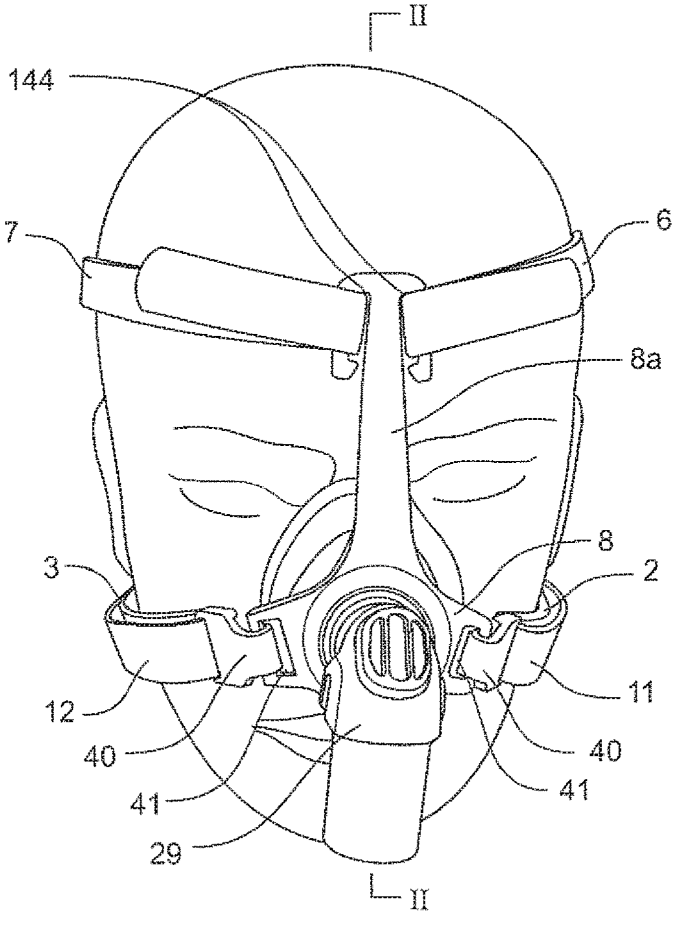
FIG. 29 is a front view of the headgear of and interface of FIGS. 26 to 28, worn by a user.
Figure 30:
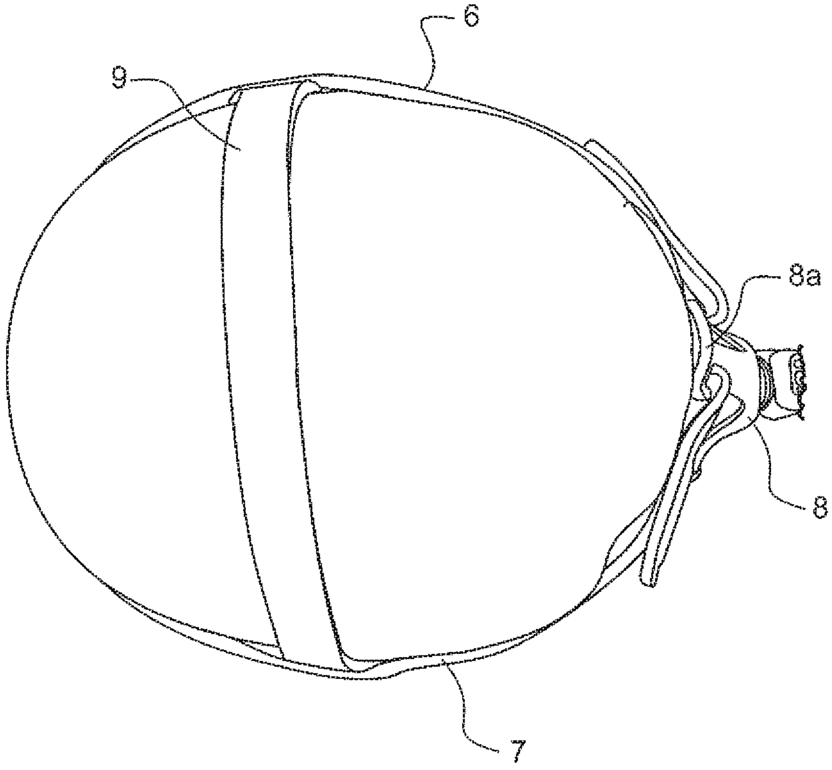
FIG. 30 is a view from above of the headgear of and interface of FIGS. 26 to 29, worn by a user.
Figure 34:
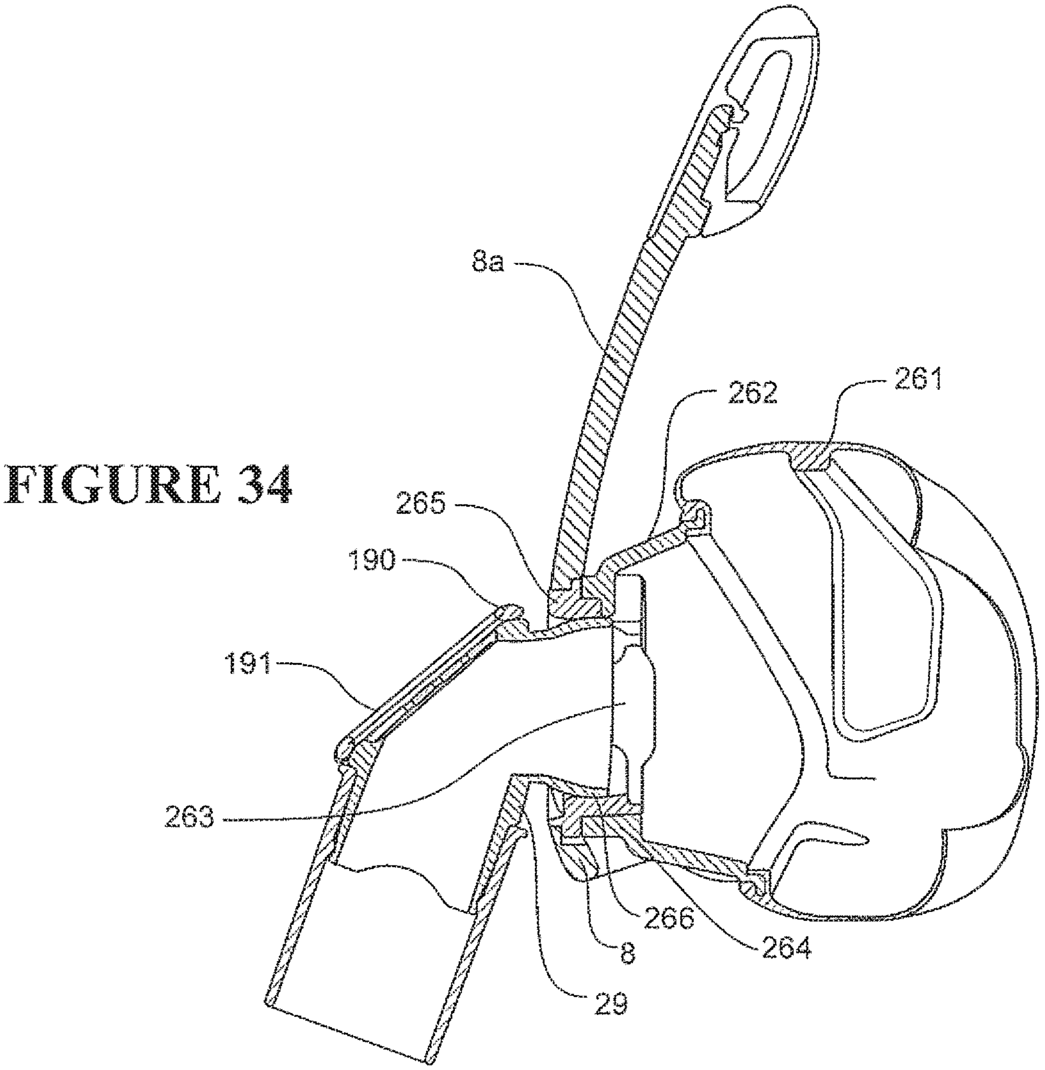
FIG. 34 is a cross-section view along line II-II of FIGS. 20 and 29, of the shell and seal, elbow, and frame, of the nasal interface of the first, fourth, and sixth embodiments of FIGS. 1 to 9, 17 to 21, and 26 to 31.

FIG. 34 is a cross-section view along line II-II of FIGS. 20 and 29, of the shell and seal, elbow, and frame, of the nasal interface of the first, third, and sixth embodiments of FIGS. 1 to 3, 17 to 22, and 26 to 31. In the embodiment shown the interface comprises seal-shell, frame, and elbow components. The soft seal 261, which may be for example a single or double flap or lip seal formed of a silicone material, is fixed to shell component 262 (to form a seal-shell component). The shell 262 comprises a gases entry opening 263 with therearound an outwardly (or alternatively inwardly) projecting annular shell collar 264. Annular mounting collar 265 is mounted into frame 8 in a suitably shaped aperture in frame 8, with a click fit or snap fit, or is welded in place, and mounting collar 265 receives annular shell collar 264 with a click fit or snap fit. The upper annular end 266 of the elbow 29 fixes into the internal diameter of mounting collar 265, for example in a click or snap fit, when the mask is assembled for use, so that the elbow is coupled to the annular mounting collar 265 (rather than to the frame or the shell). Alternatively the seal-shell component may comprise a single material seal component. Annular mounting collar 265 may be a different material and/or color to the material and/or color of frame 8.

Figure 36:
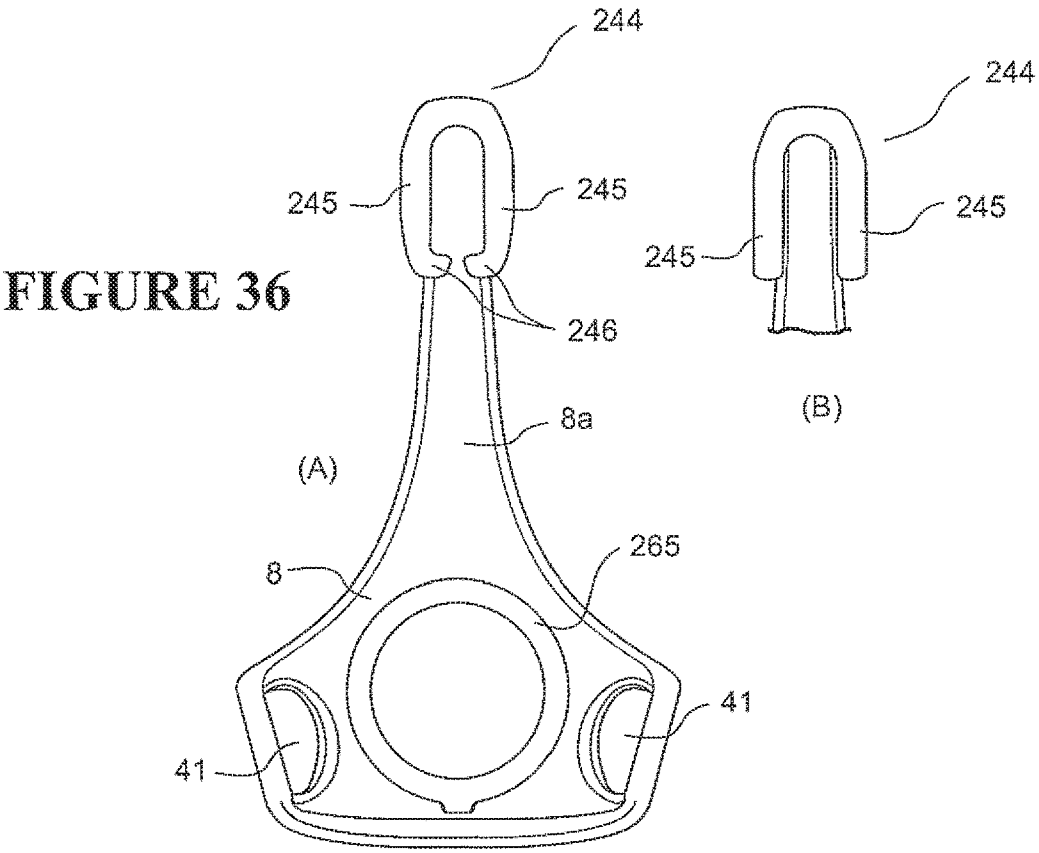
FIG. 36 is a rear view and FIG. 37 is a side view of a frame that may be used with the embodiment of FIGS. 26 to 31, and FIGS. 38A-38C schematically shows the operation of a strap of various embodiments.
Figure 37:
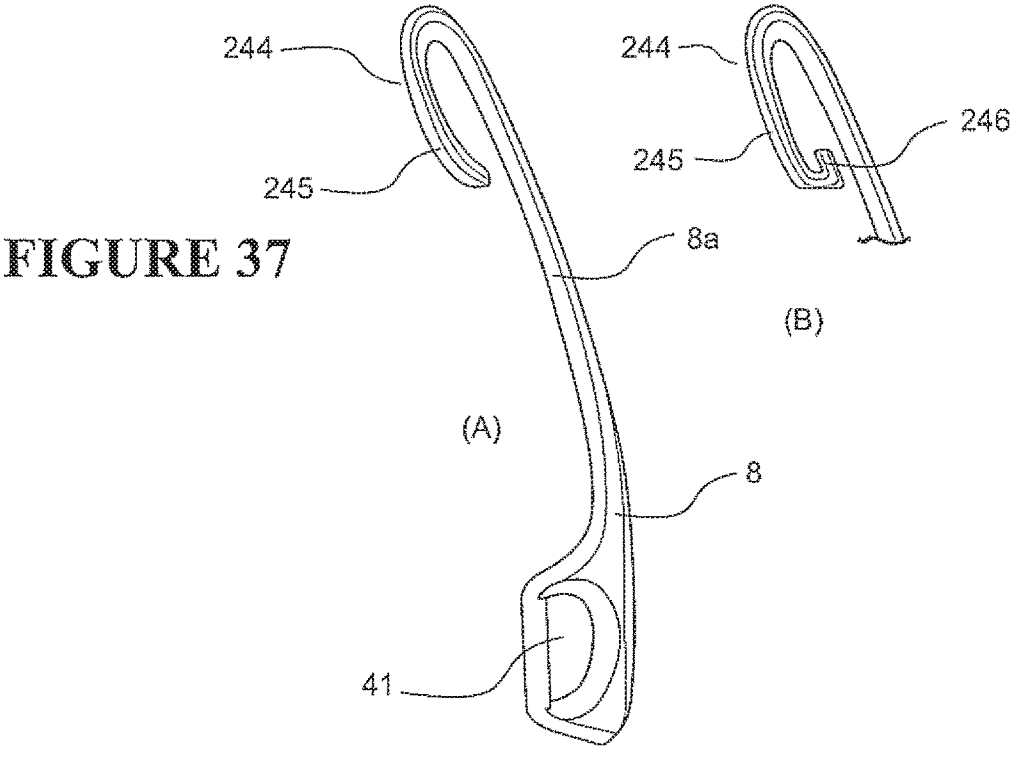

Referring to FIGS. 36 and 37, frame 8 comprises mounting collar 265, openings 41 for receiving straps and/or connectors, and forehead support 8*a*. Forehead support 8*a* comprises connector 244 for receiving the upper straps of a headgear, such as described above. Connector 244 comprises arms 245 having optional lugs 246, where lugs 246 may have different configurations (FIGS. 36A and 37A, and FIGS. 36B and 37B).

Figure 10:
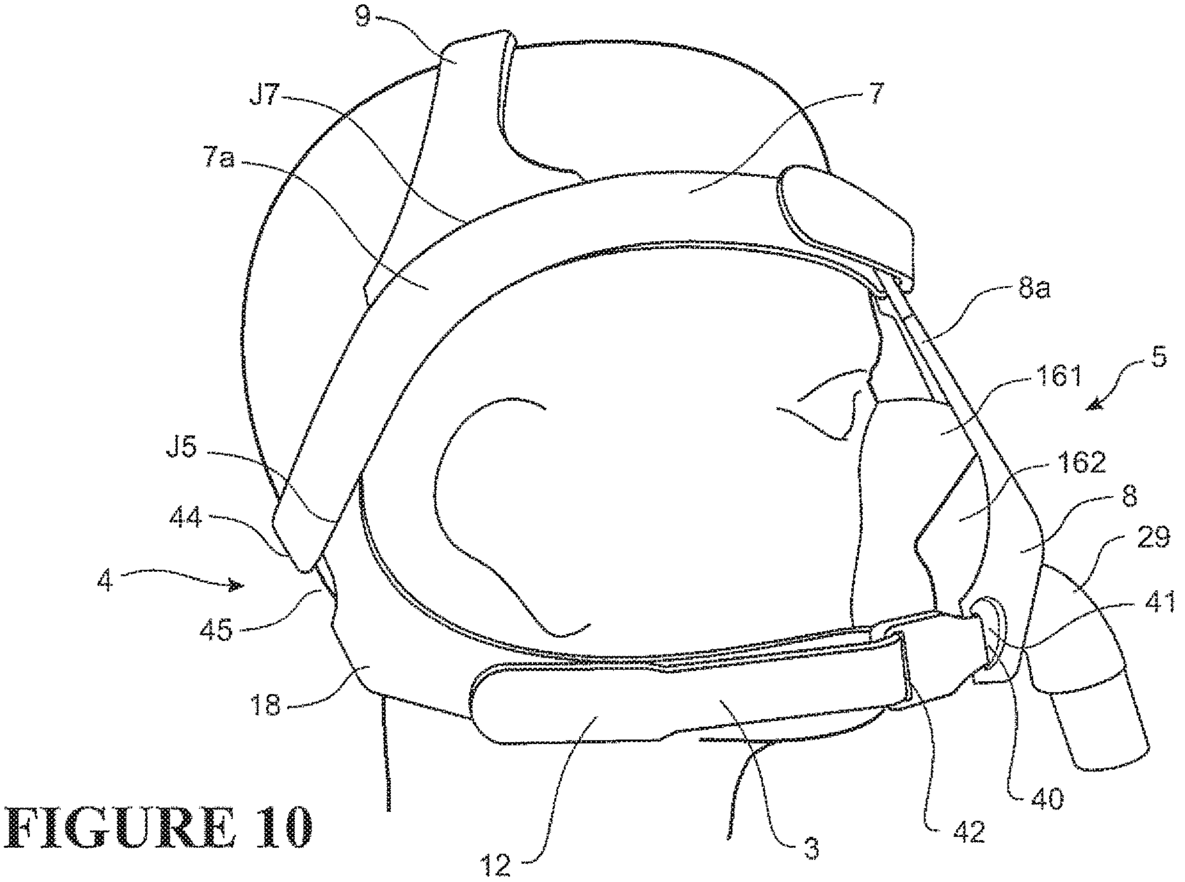
FIG. 10 is a right side view of a third embodiment of headgear of the invention, and an (Indirect) full face interface, worn by a user.
Figure 11:
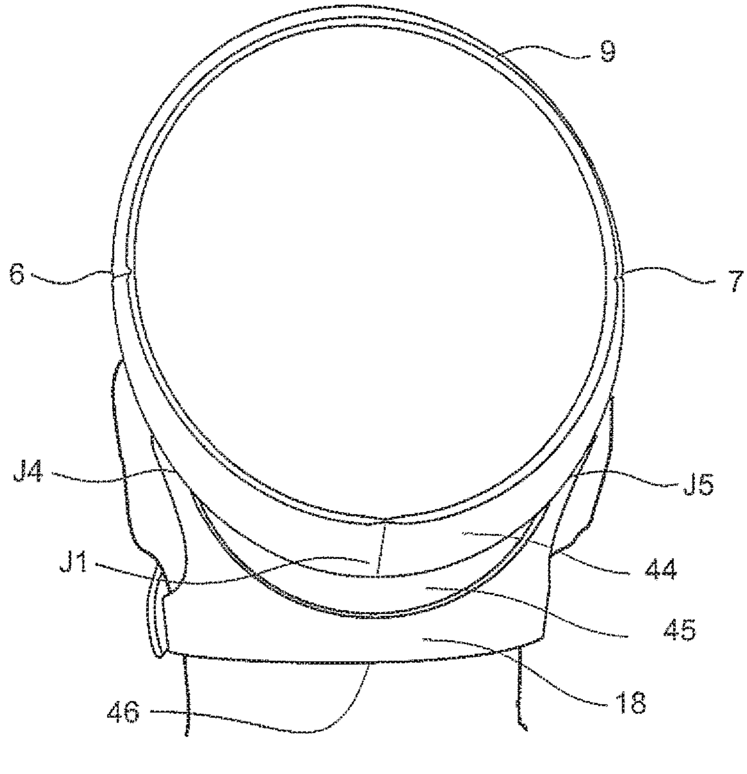
FIG. 11 is a rear view of the headgear of and interface of FIG. 10, worn by a user.
Figure 38A:
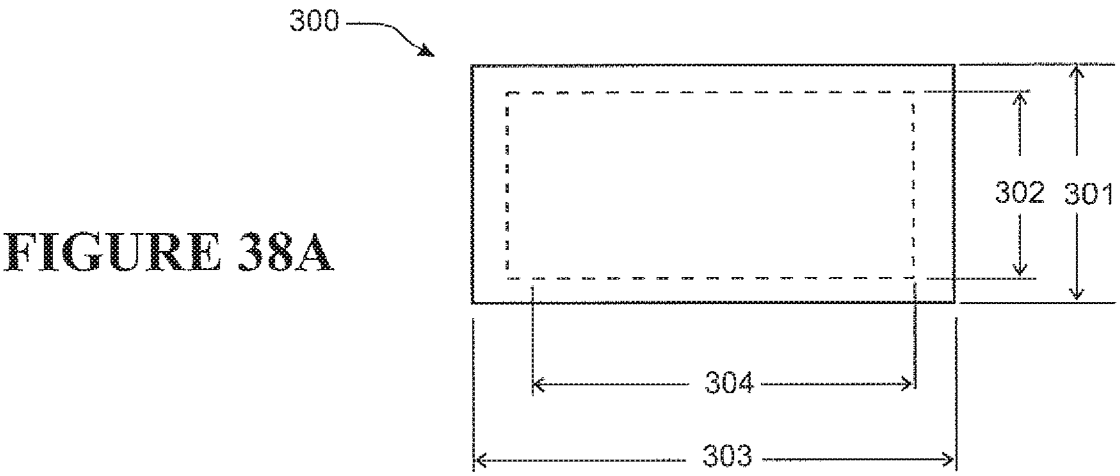
Figure 38B:
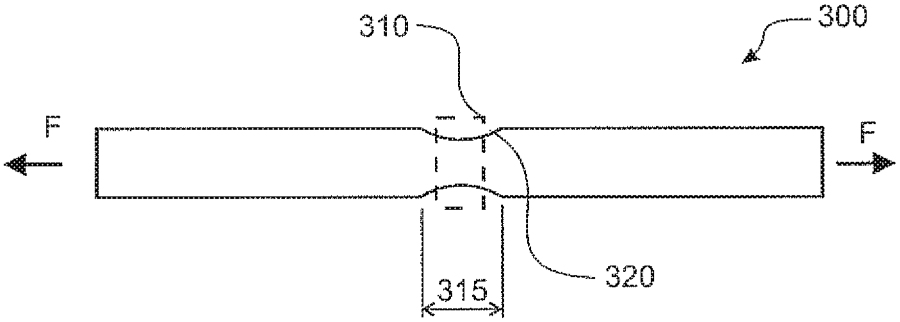
Figure 38C:
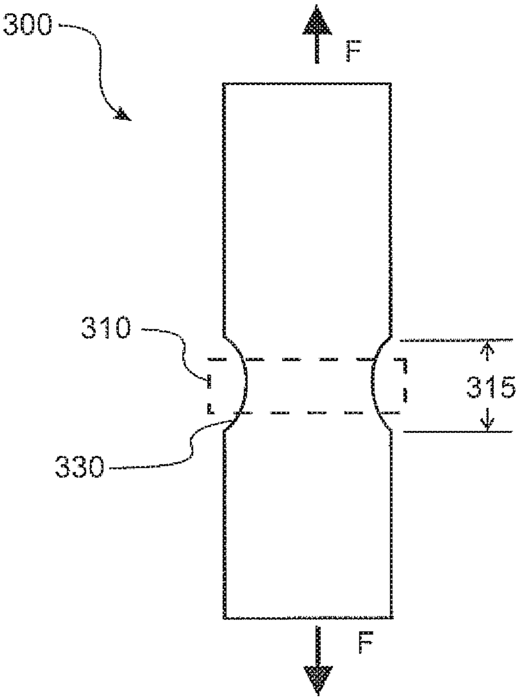

In another non-limiting exemplary embodiment, the donning or fitment of the headgear, such as any headgear described herein, including headgear for use with full face and/or nasal masks, may be further facilitated by way of friction or compressions zones created in the slot-shaped openings 42 of the hook connectors 40 (see, e.g., FIG. 10). As shown in FIGS. 38A-38C, strap 300, such as the lower straps 2 and 3 described above, have a width and/or a thickness 301,303 that is greater than the width and/or height of a slot 310, such as the slot-shaped openings 42 described above, and strap 300 is compressed to a compressed width and/or thickness 302,304 within the slot 310. As the straps 300 pass through their respective slot-shaped openings 310, the strap material is compressed 320,330, creating friction between the strap and sides and/or top and bottom of the slot-shaped opening 310. A pull force F is used to overcome the friction force and pull the strap through the slot-shaped opening.

During donning and fitment, the friction force created at the friction/compression zone 315 by slot 310 provides a resistance to movement of the strap. A user may position the mask onto the face and pull the straps to a desired tightness or fitment (see e.g., FIG. 7B). The resistance of the friction force provided by the friction/compression zone 315 fixes the mask in a temporary fitment position (i.e., prior to the straps being doubled back and Velcro attached).

In a preferred embodiment, the friction force is approximately equal to the blow-off force created by the CPAP. In such an embodiment, a user may check and adjust the fitment of the mask for leak, prior to doubling back and securing the lower straps 2 and 3. In other embodiment, the friction force may be minimal, providing enough force to maintain the mask in a temporary fitment position, without CPAP pressure.

In additional embodiments, the above friction force description may be applied to other straps and slot-shaped openings in the mask assembly.

Figure 39:
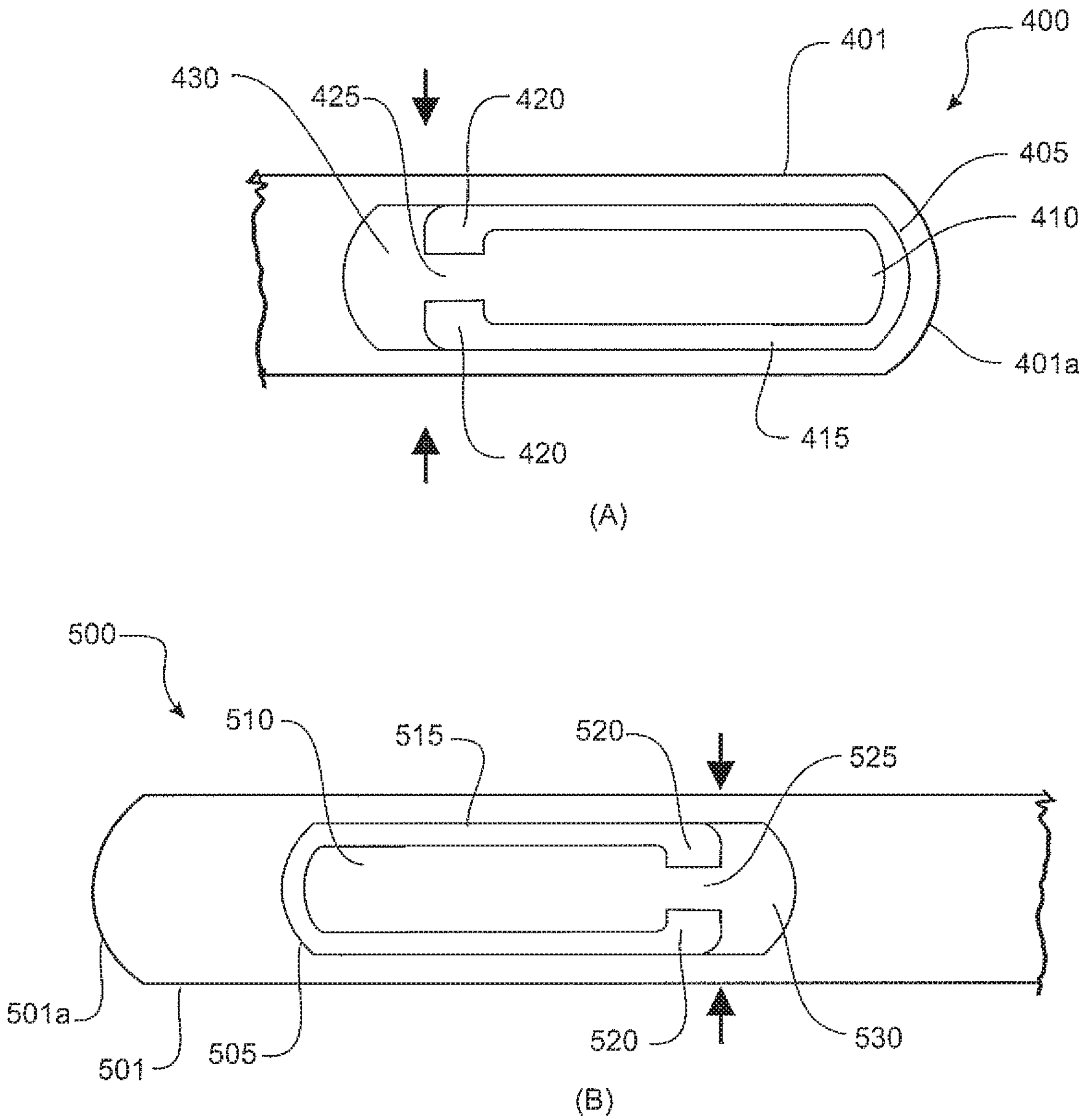
FIG. 39 is a plan view of the ends of (A) upper straps, and (B) lower straps of various embodiments.

As described above, end portions of straps used herein may comprise a section of hook material which may attach to a fabric surface layer of the straps at least on the operator side, intermediate of the strap length, to fix the strap ends when the straps are tightened, or alternatively a matching section of loop material may be provided on the strap. For example, fastening panel 187 of FIG. 25 that includes flexible tab 185 allows the strap ends to be fixed in place when the straps are tightened. FIG. 39 shows a further embodiment of such a fastening panel, located at the ends of (A) an upper side strap 400, and (B) a lower side strap 500 comprising fastening panel 405,505 with a flexible tab 430,530 that may be used in headgear of any embodiment described herein. Straps 400,500 comprise a suitable soft flexible material 401,501 such as a cloth covered foam material such a BREATH-O-PRENE™ material for example, but may be formed from other material such as in part or whole from a thermoplastic material for example. On upper side strap 400 fastening panel 405 is located displaced from end 401*a* of material 401 by a first spacing distance. On lower side strap 500 fastening panel 505 is located displaced from end 501*a* of material 501 by a second spacing distance greater than the first spacing distance, preferably great enough to allow end 501*a* to be grasped by a user without contacting or with little contact of fastening panel 505. Fastening panel 405,505 is attached to material 401,501 by a substantially U-shaped partial peripheral seal 415,515 that may be formed by gluing, stitching or welding fastening panel 405,505 in place on material 401,501, preferably welding, preferably radio frequency welding. Partial peripheral seal 415,515 is typically of consistent width except for regions 420,520 of greater area and unsealed section 425, 525. The relative arrangement of regions 420,520 and section 425,525 causes flexible tab 430,530 to extend from or stand proud of material 401,501 with memory towards that position, such as an angle of about 10 to about 900 about the virtual line indicated by arrows, to hold a position such that the flexible tab 430,530 will engage with a hook connector 40 as the strap 400,500 passes through slot-shaped opening 42 in hook connector 40, for example as shown in FIG. 25.

In use when strap 400,500 is not doubled back on itself and the strap end fixed down, flexible tab 430,530 will revert to the memorised position. Flexible tab 430,530 thus also inhibits the end of the strap being pulled out of a slot 42 in hook 40, as described for tab 185 and shown in FIG. 25B.

Other Embodiments

PC1. Headgear for a respiratory interface, including at least one strap which connects to the interface or to another strap or part of the headgear by a near end portion of the strap passing through an opening in the interface or other strap or part of the headgear, with a far end of the strap beyond the near end portion enlarged or otherwise formed to inhibit the far end of the strap being withdrawn back through the opening in the interface or other strap or part (such as connector) of the headgear.

PC2. Headgear according to PC1 wherein the far end of the strap beyond the near end comprises an enlarged protrusion or boss (herein also: hardstop) formed on the far end of the strap.

PC3. Headgear according to PC1 or PC2 wherein the strap or straps comprising the hardtop(s) also comprise on a side of said near end portion of the strap opposite said far end, a second enlargement or hardstop to inhibit the strap beyond this second hardstop passing through the opening in the interface or other strap or part of the headgear, which second hardstop is either fixed or adjustable in position along the length of the strap.

PC4. Headgear according to PC1 wherein the far end of the strap beyond the near end comprises a flexible or at least hingedly mounted tab.

PC5. Headgear according to PC1 wherein a near end portion of the strap opposite said far end comprises a flexible or at least hingedly mounted tab.

PC6. Headgear according to PC1 wherein both the far end of the strap beyond the near end and a near end portion of the strap opposite said far end each comprise a flexible or at least hingedly mounted tab.

PC7. Headgear according to any one of PC1 to PC6 wherein a rear part of the headgear is resiliently extensible.

PC8. Headgear according to any one of PC1 to PC7 comprising on each side of the headgear a structure element that maintains separation between the upper and lower straps and/or structure or 'as worn' shape to the headgear.

PC9. Headgear according to any one of PC1 to PC8 comprising resiliently extensible material attached to at least parts of the headgear or incorporated in the headgear when stretched to when relaxed provide shape to at least parts of the headgear.

PC10. Headgear according to any one of PC1 to PC9 comprising non-flat shape memory in at least a lower loop of the headgear comprising all or at least part of the lower straps and the lower rear part of the headgear.

PC11. Headgear according to any one of PC1 to PC10 comprising non-flat shape memory in at least an upper loop of the headgear.

PC12. Headgear according to any one of PC1 to PC11 wherein an upper part or parts of the headgear or a lower part or parts of the headgear or both, or an interior or exterior of the headgear or both, or any other part of the headgear, comprise a color or colors or sign contrasting to another part or parts of the headgear or a balance of the headgear or each other, which provides a visual cue to a user how the headgear with interface is to be worn or donned such as an orientation in which the headgear is to be worn or donned, or as to a top and/or bottom or an interior and/or exterior of the headgear.

PC13. Headgear for a respiratory interface, in which an upper part or parts of the headgear or a lower part or parts of the headgear or both, or an interior or exterior of the headgear or both, comprise a color or colors or sign contrasting to another part or parts of the headgear or a balance of the headgear or each other, which provides a visual cue to a user how the headgear with interface is to be worn or donned such as an orientation in which the headgear is to be worn or donned, or as to a top and/or bottom or an interior and/or exterior of the headgear.

PC14. Headgear for a respiratory interface, comprising:
- a rear part of the headgear,
- a pair of upper side straps, and
- a pair of lower side straps, composed of multiple separate sections of material joined to form the headgear, said separate sections comprising:
- two upper side strap parts which form the upper straps, each including a curved rear portion, joined at the rear of the headgear to also form an upper rear strap,
- a lower rear strap part which forms a lower rear strap; and
- two lower side strap parts which form the lower side straps and are joined to the lower rear part on left and right sides.

PC15. Headgear for a respiratory interface, comprising:
- a rear part of the headgear,
- a pair of upper side straps, and
- a pair of lower side straps, composed of multiple separate sections of material joined to form the headgear, and wherein the rear part of the headgear comprises a lower rear strap and an upper rear strap separated across the rear of the headgear by a transverse opening.

PC16. Headgear according to any one of PC14 to PC15 also comprising a top strap and wherein said separate sections include a top strap part.

The foregoing describes the invention including preferred forms thereof and alterations and modifications as will be obvious to one skilled in the art are intended to be incorporated in the scope hereof.

The invention claimed is:

1. Headgear for a respiratory interface, comprising:
- a rear part of the headgear;
- a pair of upper side straps;
- a pair of lower side straps;
- a top strap;
- a hook connector provided to each of the pair of lower side straps, the hook connector comprising a hook portion, an elongate tab and a slot-shaped opening positioned between the hook portion and the elongate tab, the hook connector having a frontmost edge defined by the hook portion, a rearmost edge defined by the elongate tab, and a length direction extending between the frontmost edge and the rearmost edge, the hook portion defining an arcuate portion that curves around an axis that is perpendicular to the length direction, the hook portion having a free end located between the frontmost edge and the rearmost edge, the elongate tab including a gripping surface that is elongate in the length direction;
- each of the lower side straps being configured to pass through the respective slot-shaped opening, fold back on itself, and affix to itself, forming a strap loop such that the elongate tab of the hook connector provided to each of the pair of lower side straps lies within a respective strap loop and the length direction of the hook connector is aligned with a length direction of the respective lower side strap, wherein the elongate tab of the hook connector provided to each of the pair of lower side straps together with a respective folded strap is configured to be grasped to engage or disengage the hook connector; and wherein a first distance in the length direction between the rearmost edge of the hook connector and a rear edge of the slot-shaped opening is greater than a second distance in the length direction between the rear edge of the slot-shaped opening and a rearmost edge of the free end of the hook portion.

2. The headgear of claim 1, wherein one or more straps of the pair of upper side straps and one or more of the pair of lower side straps comprise a far end portion comprising a flexible or at least hingedly mounted tab.

3. The headgear of claim 2, wherein the flexible or at least hingedly mounted tab is an extension of a plastic backing material of a hook and loop fastening panel.

4. The headgear of claim 1, wherein one or more straps of the pair of upper side straps and one or more of the pair of lower side straps comprise a near end portion comprising a flexible or at least hingedly mounted tab.

5. The headgear of claim 4, wherein the flexible or at least hingedly mounted tab is an extension of a plastic backing material of a hook and loop fastening panel.

6. The headgear of claim 1, wherein one or more straps of the pair of upper side straps and one or more of the pair of lower side straps comprise a far end portion and a near end portion, each portion comprising a flexible or at least hingedly mounted tab.

7. The headgear of claim 6, wherein the flexible or at least hingedly mounted tab is an extension of a plastic backing material of a hook and loop fastening panel.

8. The headgear of claim 1, wherein the hook portion is shaped to provide a wide angle of engagement with a corresponding slot on a frame of a patient interface.

9. The headgear of claim 1, wherein the pair of upper side straps and the pair of lower side straps comprise end portions provided with a hook material, and wherein the pair of upper side straps and the pair of lower side straps comprise intermediate portions provided with a corresponding section of loop material.

10. The headgear of claim 1, wherein a secondary hook connector is provided to each of the pair of upper side straps, the secondary hook connector comprising a hook portion, a slot-shaped opening, and an elongate tab.

11. The headgear of claim 1, wherein the pair of lower side straps comprise end portions, the end portions configured to inhibit the end portions from being drawn through the slot-shaped opening.

12. The headgear of claim 11, wherein the end portions comprise an enlarged protrusion or boss.

13. The headgear of claim 12, wherein the pair of lower side straps are formed from a soft flexible material and the enlarged protrusion or boss is formed from a material harder than the soft flexible material.

14. The headgear of claim 11, wherein the end portions are enlarged perpendicular to a plane of the pair of upper side straps and the pair of lower side straps when the pair of upper side straps and the pair of lower side straps are laid out flat.

15. The headgear of claim 11, wherein at least one strap of the pair of lower side straps further comprises a clip that is adjustable in position between ends of the at least one strap.

16. The headgear of claim 1, wherein one or more straps of the pair of lower side straps is wider than a width of the slot-shaped opening.

17. The headgear of claim 1, wherein the headgear comprises at least four different levels of stretchability in at least four different parts or straps of the headgear, the top strap has a highest level of stretchability, and the pair of lower side straps have a lowest level of stretchability or are substantially non-stretchable.

18. The headgear according to claim 17, wherein the rear part of the headgear comprises a lower rear strap and an upper rear strap separated across the rear part of the headgear by a transverse opening.

19. The headgear of claim 1, wherein the elongate tab comprises a thickness extending between a first surface and a second surface opposite the first surface, wherein the first surface faces towards a patient's face in use, and wherein a length and a width of the elongate tab are greater than the thickness of the elongate tab.

20. A respiratory interface comprising:

a seal or a seal-shell, a frame, and elbow components;

a headgear comprising:

a rear part of the headgear, a pair of upper side straps, a pair of lower side straps, a top strap, and a hook connector provided to each of the pair of lower side straps, the hook connector comprising a hook portion, an elongate tab, and a slot-shaped opening positioned between the hook portion and the elongate tab, the hook connector having a frontmost edge defined by the hook portion, a rearmost edge defined by the elongate tab, and a length direction extending between the frontmost edge and the rearmost edge, the elongate tab includes a gripping surface that is elongate in the length direction;

each of the lower side straps being configured to pass through the respective slot-shaped opening, fold back on itself, and affix to itself, forming a strap loop such that the elongate tab of the hook connector provided to each of the pair of lower side straps lies within a respective strap loop and the length direction of the hook connector is aligned with a length direction of the respective lower side strap, wherein the elongate tab of the hook connector provided to each of the pair of lower side straps together with a respective folded strap is configured to be grasped to engage or disengage the hook connector;

wherein the headgear comprises at least four different levels of resilient extensibility or stretchability in at least four different parts or straps of the headgear, the top strap has a highest level of stretchability, and the pair of lower side straps have a lowest level of stretchability or are substantially non-stretchable; and wherein the slot-shaped opening is positioned a distance from the rearmost edge, wherein an elongate tab length, which is a distance between the slot-shaped opening and the rearmost edge, is greater than a thickness of the elongate tab.

21. The respiratory interface according to claim 20, the frame comprising:

a seal or a seal-shell mounting collar, one or more openings for receiving the hook portion of the hook connector, and a forehead support comprising a connector for receiving the pair of upper side straps of the headgear, the connector comprising two substantially parallel arms that project rearwardly in a user-direction and extend in a downward direction, a longitudinal slot being defined adjacent each arm, each longitudinal slot comprising an opening at a lower end thereof.

22. The respiratory interface according to claim 21, wherein each arm comprises a lug that projects at least partially into the longitudinal slot.

23. The respiratory interface according to claim 20, wherein each hook connector provided to each of the pair of lower side straps has an outer surface configured to face away from a patient in use and a connector length defined between the frontmost edge and the rearmost edge of the outer surface of the hook connector, a respective elongate tab of each hook connector has an elongate tab length that is at least half of the connector length and the elongate tab length forming a portion of the connector length.

24. The respiratory interface of claim 20, wherein a width of the elongate tab is greater than the thickness of the elongate tab.

* * * * *